United States Patent
Ledet et al.

(10) Patent No.: US 10,105,235 B2
(45) Date of Patent: Oct. 23, 2018

(54) INTERVERTEBRAL CAGE AND METHOD OF TREATING VERTEBRAE WITH AN INTERVERTEBRAL CAGE

(71) Applicant: REVIVO MEDICAL, LLC, Schenectady, NY (US)

(72) Inventors: Eric H. Ledet, Schenectady, NY (US); Glenn Patrick Sanders, Sand Lake, NY (US)

(73) Assignee: REVIVO MEDICAL, LLC, Schenectady, NY (US)

( * ) Notice: Subject to any disclaimer, the term of this patent is extended or adjusted under 35 U.S.C. 154(b) by 498 days.

(21) Appl. No.: 14/776,988

(22) PCT Filed: Mar. 17, 2014

(86) PCT No.: PCT/US2014/030596
§ 371 (c)(1),
(2) Date: Sep. 15, 2015

(87) PCT Pub. No.: WO2014/145774
PCT Pub. Date: Sep. 18, 2014

(65) Prior Publication Data
US 2016/0030194 A1    Feb. 4, 2016

Related U.S. Application Data

(60) Provisional application No. 61/852,079, filed on Mar. 15, 2013.

(51) Int. Cl.
*A61F 2/44* (2006.01)
*A61F 2/30* (2006.01)
*A61F 2/28* (2006.01)

(52) U.S. Cl.
CPC .............. *A61F 2/4455* (2013.01); *A61F 2/44* (2013.01); *A61F 2/442* (2013.01);
(Continued)

(58) Field of Classification Search
CPC .......... A61F 2/44; A61F 2/442; A61F 2/4425; A61F 2/4455; A61F 2/446; A61F 2/4465;
(Continued)

(56) References Cited

U.S. PATENT DOCUMENTS 5,554,191 A    9/1996  Lahille
5,645,599 A *  7/1997  Samani .............. A61B 17/7062
                                                       606/248
(Continued)

FOREIGN PATENT DOCUMENTS

EP    1099428 A2    5/2001
FR    2812806 A     8/2000
(Continued)

OTHER PUBLICATIONS

Extended European Search Report completed by the EPO for European Patent Application No. 14763706.0 and attached to Rules 70(2) and 70a(2) communication dated Nov. 26, 2016.
(Continued)

*Primary Examiner* — Eric S Gibson
(74) *Attorney, Agent, or Firm* — Heslin Rothnberg Farley & Mesiti P.C.

(57) ABSTRACT

The present disclosure provides an intervertebral cage including superior and inferior members each including an engagement surface for engaging a corresponding vertebrae. The intervertebral cage also includes a posterior member that extends between a posterior end of the superior and inferior members and spaces them from each other in a superior-inferior direction. The superior and inferior members extend in a posterior-to-anterior direction from the posterior member and define anterior free ends to form a substantially open anterior end between the superior member and the inferior member in a posterior-anterior direction. The engagement surfaces of the superior and inferior mem-
(Continued)

bers substantially diverge from each other in the superior-inferior direction along the posterior-to-anterior direction. The superior and inferior members each include first apertures extending therethrough in the superior-inferior direction that define a pathway through the intervertebral cage in the superior-inferior direction.

37 Claims, 18 Drawing Sheets

(52) U.S. Cl.
CPC ............ *A61F 2002/2835* (2013.01); *A61F 2002/30018* (2013.01); *A61F 2002/30131* (2013.01); *A61F 2002/30563* (2013.01); *A61F 2002/30565* (2013.01); *A61F 2002/30578* (2013.01); *A61F 2002/30787* (2013.01); *A61F 2002/30904* (2013.01); *A61F 2310/00023* (2013.01); *A61F 2310/00359* (2013.01)

(58) Field of Classification Search
CPC ............ A61F 2/447; A61F 2002/443; A61F 2002/4475
See application file for complete search history.

(56) References Cited

U.S. PATENT DOCUMENTS

| | | | | |
|---|---|---|---|---|
| 6,102,950 | A * | 8/2000 | Vaccaro | A61F 2/4611 606/247 |
| 7,815,663 | B2 * | 10/2010 | Trieu | A61B 17/7026 606/254 |
| 9,872,777 | B2 * | 1/2018 | Ganter | A61F 2/442 |
| 2004/0006343 | A1 * | 1/2004 | Sevrain | A61B 17/7059 606/279 |
| 2005/0125063 | A1 * | 6/2005 | Matge | A61F 2/442 623/17.13 |
| 2006/0265068 | A1 * | 11/2006 | Schwab | A61B 17/7067 623/17.11 |
| 2007/0173938 | A1 | 7/2007 | Sweeney | |
| 2007/0191953 | A1 * | 8/2007 | Trieu | A61F 2/442 623/17.15 |
| 2007/0225806 | A1 * | 9/2007 | Squires | A61F 2/442 623/17.11 |
| 2008/0119933 | A1 | 5/2008 | Aebi et al. | |
| 2010/0234956 | A1 | 9/2010 | Attia et al. | |
| 2010/0286777 | A1 * | 11/2010 | Errico | A61F 2/442 623/17.11 |
| 2011/0153020 | A1 | 6/2011 | Abdelgany et al. | |
| 2011/0313528 | A1 | 12/2011 | Laubert et al. | |
| 2014/0309741 | A1 * | 10/2014 | Ganter | A61F 2/442 623/17.16 |
| 2016/0030194 | A1 * | 2/2016 | Ledet | A61F 2/44 623/17.16 |

FOREIGN PATENT DOCUMENTS

| | | |
|---|---|---|
| JP | H07213533 | 8/1995 |
| WO | 9907312 A1 | 2/1999 |
| WO | 200162190 A1 | 8/2001 |
| WO | 2008132322 A2 | 11/2008 |
| WO | 2009129605 A1 | 10/2009 |
| WO | 2010137110 A1 | 12/2010 |

OTHER PUBLICATIONS

Sep. 15, 2015: International Report on Patentability for International Application No. PCT/US2014/030596.
International Search Report for PCT/US14/30596 dated Nov. 7, 2014.

* cited by examiner

INTERVERTEBRAL CAGE AND METHOD OF TREATING VERTEBRAE WITH AN INTERVERTEBRAL CAGE

CROSS REFERENCE TO RELATED APPLICATIONS

This application is a national stage filing under section 371 of International Application No. PCT/US2014/030596 filed on Mar. 17, 2014, and published in English on Sep. 18, 2014 as WO 2014/145774 A2 and claims priority to U.S. Provisional Patent Application No. 61/852,079, filed on Mar. 15, 2013, entitled Dynamic Modular Cage-Plate Device, the entire disclosure of these applications being hereby incorporated herein by reference.

BACKGROUND

The present disclosure generally relates to devices and methods that provide structural support to aspects of a spine, and in particular to deformable intervertebral cages and related methods that facilitate arthrodesis and/or interbody fusion and/or dynamic stabilization of a motion segment of a spine.

Spinal pathology and surgery are common practices with patients with spinal cord compression and/or nerve root compression when conservative treatments have failed. The current standard and most commonly utilized procedure in the spine is an anterior cervical discectomy and fusion (ACDF). Commonly, in ACDF one or multiple levels of the cervical spine are exposed from an anterior approach. The spine is then distracted and discectomy and decompression are performed. A bone graft or interbody implant (referred to as a "cage") is often placed to fill the vacated disc space and to assist in maintaining disc height.

Intervertebral cages typically serve two main purposes. First, some vertebral interbody cages may act as a containment device for a bone graft. Secondly, some vertebral interbody cages may fill a vertebral body defect or an intervertebral defect and, potentially, resist axial loading of the spine. In the cervical, thoracic and lumbar regions of the spine, corpectomies, or removal of the vertebrae, is often performed, such as in cases of degenerative disease, trauma (burst fractures), tumors of the spine, and infections of the disc and vertebrae. In such cases, an intervertebral cage is usually inserted from the anterior or lateral regions of the vertebrae, though they may be applied through a posterior approach.

In typical practice, once an intervertebral cage is implanted between adjacent endplates of the spine, a spinal fixation plate is used to stabilize the spine and to foster arthrodesis. Spinal fixation plates may span a single intervertebral disc and affix to two adjacent vertebrae for a single level procedure. Multiple level applications may also be performed. Most commonly, spinal fixation plates are affixed to the vertebrae using bone fixation devices, such as bone screws.

While static bone plates may be effective at stabilizing the spine in some applications, the inventors have appreciated that they may cause graft stress shielding, graft overloading, subsidence, and/or graft failure. Another common complication associated with plate fixation in the spine, such as in the cervical spine, following anterior interbody arthrodesis is dysphagia. Dysphagia is commonly caused by irritation of the esophagus and surrounding tissue due to the implant which may extend at least partially out of the intervertebral disc space. In some embodiments, dynamic plate implants have been designed to provide load sharing during flexion/extension of the spine to minimize graft over-loading and/or promote loading through the bone graft.

All-in-one cage-plate implants may provide some of the advantages of plating including resistance to flexion-extension motion, lateral bending motion, and torsion. Cage-plate implants may also provide the advantages of cages including resistance to flexion (compression) and support for bone graft. The goal of these devices is to stabilize the spine to facilitate bony fusion. However, typical cage-plates are formed of static components that are fraught with the complications associated with static plate fixation, namely graft stress shielding, graft overloading, subsidence, and graft failure. Graft stress shielding or graft overloading can lead to fibrous tissue formation or bone resorption, ultimately resulting in pseudarthrosis. For example, excessive strain on a bone graft and forming bone may lead to a fibrous non-union. As another example, inadequate strain on a bone graft and forming bone may facilitate primary bone formation and not facilitate secondary bone formation. Excessive micromotion may also lead to bone resorption and pseudarthrosis. Micromotion which exceeds 100 microns can lead to osteolysis and loss of osseointegration.

Total disc replacement is an alternative to arthrodesis for some patients with spinal degeneration. However, total disc replacement has different goals than arthrodesis and fusion. Total disc replacements attempt to return the disc to physiologic motion including flexion, extension, lateral bending, and torsion. Disc replacement devices are often structured to prohibit bony throughgrowth to facilitate long term motion preservation of the spinal motion segment As a result, a need exists for devices and methods that utilize a bone graft and provide for the appropriate balance of facilitating load sharing while eliminating/reducing stress shielding and micro-motion to achieve vertebral arthrodesis and/or fusion.

BRIEF DESCRIPTION

In accordance with one aspect of the present disclosure, an intervertebral cage is disclosed. The intervertebral cage includes a superior member including a first engagement surface for engaging a superior vertebrae. The intervertebral cage further includes an inferior member including a second engagement surface for engaging an inferior vertebrae. The intervertebral cage further includes a posterior member extending between a first end of the superior member and a first end of the inferior member. The posterior member spaces the first ends of the superior member and the inferior member in a superior-inferior direction. The superior member and the inferior member extend in a posterior-to-anterior direction from the posterior member and define anterior free second ends to form a open anterior end between the superior member and the inferior member in a posterior-anterior direction. The first engagement surface of the superior member and the second engagement surface of the inferior member substantially diverge from each other in the superior-inferior direction along the posterior-to-anterior direction from the posterior member to the free second ends thereof. The superior member and the inferior member each include first apertures extending therethrough in the superior-inferior direction that at least partially overlap in the superior-inferior direction and define a first pathway through the intervertebral cage in the superior-inferior direction.

In accordance with one aspect of the present disclosure, a method of treating a superior vertebral body and an inferior vertebral body is disclosed. The superior and inferior vertebral bodies are proximate a spinal canal in an anterior direction. The method includes positioning a first engagement surface of a superior member of an intervertebral cage proximate the superior vertebral body, a second engagement surface of an inferior member of the intervertebral cage proximate the inferior vertebral body, and a posterior member of the intervertebral cage extending between a first end of the superior member and a first end of the inferior member in a superior-inferior direction proximate the spinal cord. The superior member and the inferior member extend in a posterior-to-anterior direction from the posterior member and define anterior free second ends to form a substantially open anterior end between the superior member and the inferior member in a posterior-anterior direction. The superior member and the inferior member each include first apertures extending therethrough in the superior-inferior direction that at least partially overlap in the superior-inferior direction to define a first pathway from the superior vertebral to the inferior vertebral through the intervertebral cage in the superior-inferior direction. The first and second engagement surfaces substantially diverge in the posterior-to-anterior direction from the posterior member to the free second ends thereof. The method further includes securing the superior member of the intervertebral cage to the superior vertebral body. The method further includes securing the inferior member of the intervertebral cage to the inferior vertebral body.

These and other objects, features and advantages of this disclosure will become apparent from the following detailed description of the various aspects of the disclosure taken in conjunction with the accompanying drawings.

DRAWINGS

DETAILED DESCRIPTION

Figure 1:
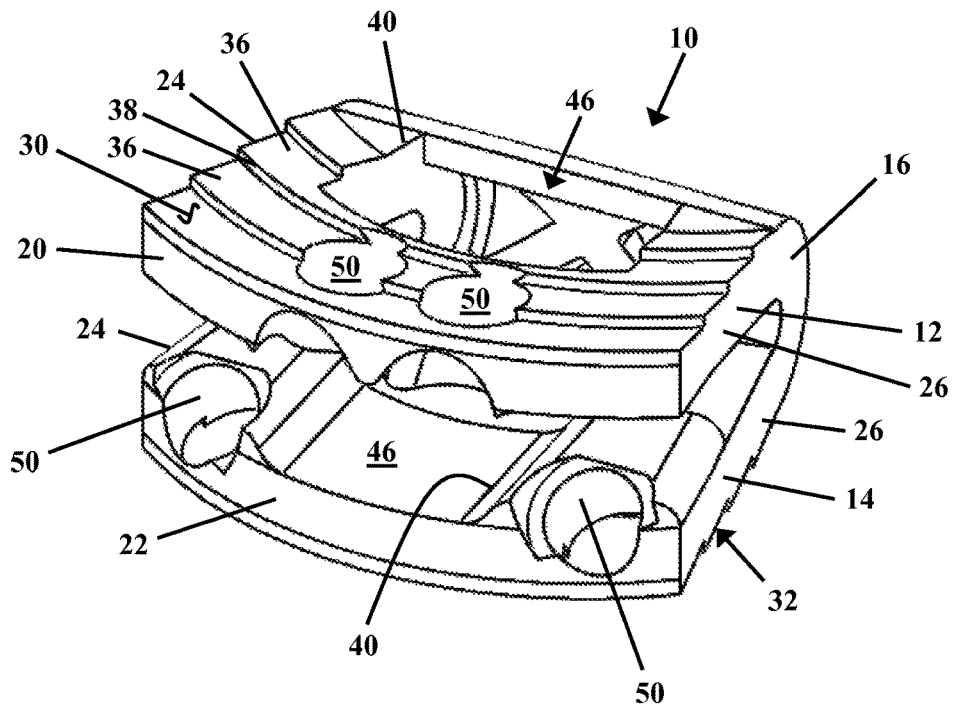
FIG. 1 is a superior perspective view of a first exemplary embodiment of an intervertebral cage of the present disclosure.
Figure 2:
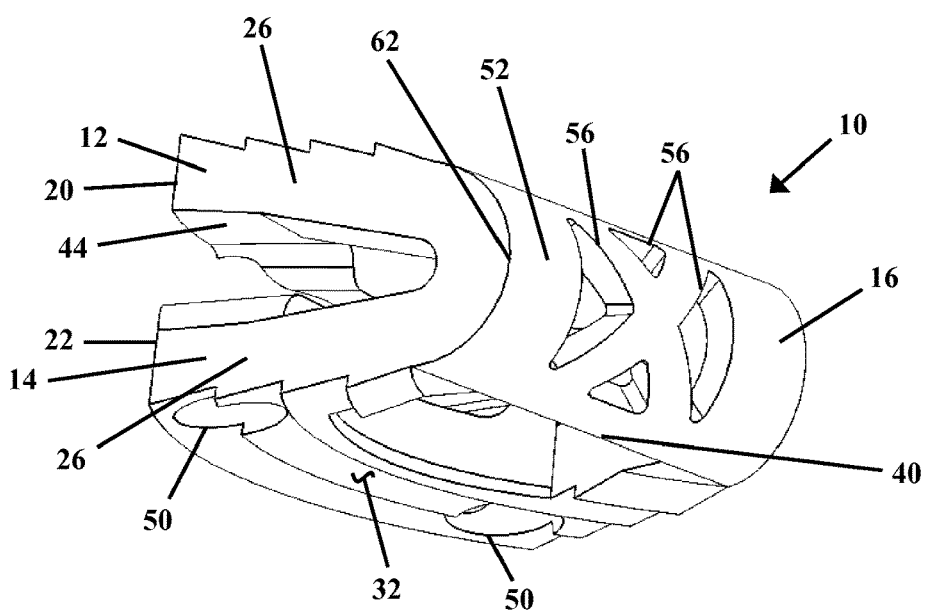
FIG. 2 is a inferior perspective view of the first exemplary intervertebral cage of the present disclosure.

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

In this application, including the claims, the terms proximal, distal, anterior, posterior, medial, lateral, superior, inferior, cranial and caudal are defined by their standard usage for indicating a particular aspect or orientation of a bone, other anatomy, implant, device or the like according to the relative disposition of the natural anatomy or directional terms of reference with respect thereto, as is known by ordinary skill in the art. For example, "proximal" means the portion of an implant or anatomy nearest a relative aspect, while "distal" indicates the portion of the implant or anatomy farthest from a relative aspect. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another aspect.

The present disclosure provides apparatus, devices, systems, components and related methods which may provide structural support to one or more levels of the spine (e.g., cervical, thoracic, or lumbar spine) to achieve vertebral or spine arthrodesis and/or interbody fusion. In some embodiments, the apparatus, devices, systems, components and related methods of the present disclosure are particular advantageous for use with the cervical spine. In some embodiments, the apparatus, devices, systems, components and related methods of the present disclosure are particular advantageous for use with the lumbar spine.

In some embodiments, the present disclosure provides a deformable (e.g., elastically) interbody or intervertebral cage (referred to herein as either "intervertebral cage" or simple "cage"). In some embodiments, the intervertebral cage may be configured to be positioned between adjacent vertebral bodies. For example, in some embodiments the intervertebral cage may be configured to be positioned between endplates. As another example, in some embodiments the intervertebral cage may be configured to be positioned between non-modified vertebral bodies (i.e., vertebral bodies in their natural occurring state or condition). As still another example, in some embodiments the intervertebral cage may be configured to be positioned between resected or otherwise modified vertebral bodies (i.e., modified from their natural occurring state or condition (e.g., a corpectomy)).

In some embodiments, the present disclosure provides an intervertebral cage that may be elastically deformable to allow load sharing during mechanical loading of the spine in which it is implanted. In some embodiments, the intervertebral cage is configured to facilitate arthrodesis and interbody fusion while utilizing a bone graft. For example, in some embodiments, the intervertebral cage may be configured to utilize a bone graft and provide for the appropriate balance of facilitating load sharing while eliminating/reducing stress shielding and micro-motion to achieve vertebral or spine arthrodesis and/or fusion. In some embodiments, the intervertebral cage facilitates dynamic stabilization of a motion segment. In some embodiments, the intervertebral cage may include relatively rigid sections for affixing the cage to vertebrae (e.g., endplates) and elastically deformable section(s) between the rigid sections for fostering controlled deformation that provides load sharing while eliminating/reducing stress shielding and micro-motion to facilitate arthrodesis and/or fusion.

In some embodiments, the present disclosure provides an intervertebral cage that is sized, shaped and otherwise configured or constructed such that it can be applied through a substantially limited open incision (or substantially minimally invasively). In some embodiments, the intervertebral cage may be sized, shaped and otherwise configured or constructed such that it can be implanted as a substantially one-step mechanism.

In some embodiments, the intervertebral cage may be sized, shaped and otherwise configured or constructed such that it defines a relatively low profile. For example, in some embodiments, the intervertebral cage may be sized, shaped and otherwise configured or constructed such that it is substantially or entirely contained between adjacent vertebral bodies. Stated differently, in some embodiments the intervertebral cages of the present disclosure may be sized, shaped and otherwise configured or constructed such that they are contained completely within the disc space between vertebral bodies. For example, the profile of the vertebral bodies along the medial-lateral and anterior-posterior directions may be larger than that of the intervertebral cage (i.e., the intervertebral cage may not extend past the vertebral bodies when viewed along the superior-inferior direction). The relatively low profile nature of intervertebral cages of the present disclosure is particularly advantageous as critical anatomical structures lie in close proximity to the ventral and lateral aspect of vertebrae. These structures include the esophagus, the iliac arteries and veins, the sympathetic chain, the psoas muscle, and the lumbar plexus. The relatively low profile nature of the intervertebral cages of the present disclosure prevents irritation or damage to these structures, for example.

As discussed above, the present disclosure provides for intervertebral cages that are configured to utilize a bone graft and provide for the appropriate balance of facilitating load sharing while eliminating/reducing stress shielding and micro-motion to achieve vertebral or spine arthrodesis and/or fusion. In some embodiments, the intervertebral cages may be elastically deformable in compression or extension when the spine moves in flexion, extension, or lateral bending. In some embodiments, an axial load may compress the cage and thereby allow for controlled elastic deformation which fosters load sharing with, for example, a graft. In some embodiments, in flexion, extension, and lateral bending, the exemplary cages may mate with vertebral bodies (e.g., endplates) and allow minimal liftoff, space or gap between the cages and the vertebral bodies.

In some embodiments, the intervertebral cages may prevent stress shielding or overloading, and thereby fibrous tissue formation or bone resorption which may result in pseudarthrosis. For example, in some embodiments the intervertebral cages may be configured to substantially prevent or reduce the occurrence of strains less than about 2% (e.g., about 2,000 microstrain) and exceeding about 10% as a result of normal or typical physiologic loading conditions to bone forming between the vertebral bodies in which an intervertebral cage is implanted (e.g., bone forming between the vertebral bodies and a bone graft positioned at least partially within the intervertebral cage). In some embodiments, the intervertebral cages may be substantially stiffer in torsion to minimize rotation of the motion segment and micro-motion at the interfaces between the cage and the vertebrae. In some embodiments, the intervertebral cages may allow for no more than about 100 microns of motion during normal physiologic loading to facilitate longevity of the implant. In some embodiments the intervertebral cage may be configured to substantially prevent or reduce stress shielding or overloading and substantially facilitate load sharing motion (e.g., strain) within the range of about 2% to about 10%, and limit micro-motion to less than about 100 microns.

In some embodiments, the intervertebral cage, or components thereof, may substantially be Ti6Al4V, or other titanium or titanium alloys. In some embodiments, the intervertebral cage, or components thereof, may substantially be a metal, polymer, bone, ceramic, or a composite material. In some embodiments, the intervertebral cage, or components thereof, may be a carbon fiber polyether-ether ketone (PEEK) composite. In some embodiments, the intervertebral cage, or components thereof, may be integral, of one-piece construction or monolithic.

As shown in FIGS. 1-12, in one exemplary embodiment the exemplary cage 10 may include an superior member or portion 12, an exemplary inferior member or portion 14, and a posterior member 16 or portion 16 extending between a first end of the superior member 12 and a first end of the inferior member 14. The cross-section of the posterior member 16, superior member 12, and inferior member 14 in the medial-lateral, anterior-posterior and superior-inferior directions may be circular, elliptical, square, rectangular, or another uniform or non-uniform geometric shape or configuration. The posterior member 16 may space the first ends of the superior member 12 and the inferior member 14 in a superior-inferior direction. For example, the posterior member 16 may extend at least in the superior-inferior direction and the superior member 12 and the inferior member 14 may extend from (or be coupled to) opposing sides or ends of the posterior member 16 in the superior-inferior direction. Specifically, as shown in FIGS. 1-12, in some embodiments the superior member 12 and the inferior member 14 extend in a posterior-to-anterior direction from the posterior member 16 and define anterior free second ends 20, 22.

In some embodiments the free second ends 20, 22 of the superior member 12 and the inferior member 14 may be spaced in the superior-inferior direction and otherwise form a substantially open anterior end between the superior member 12 and the inferior member 14 in a posterior-anterior direction. Stated differently, in some embodiments the superior member 12 and the inferior member 14 are not attached anteriorly. In this way, the superior member 12 and the inferior member 14 may each be provided as cantilever beam-type members. In some embodiments, the open anterior end may allow for access, both visually and physically, into the interior of the cage 10 between the superior member 12 and the inferior member 14. For example, the open anterior end may allow for an anterior-to-posterior view into and through the cage 10 between the superior member 12 and the inferior member 14 in the superior-inferior direction, as explained further below. As another example, the open anterior end may allow for anterior-to-posterior translation of at least one object (e.g., graft material, resilient element(s), etc.) into the cage 10 between the superior member 12 and the inferior member 14 in the superior-inferior direction, as explained further below.

Figure 7:
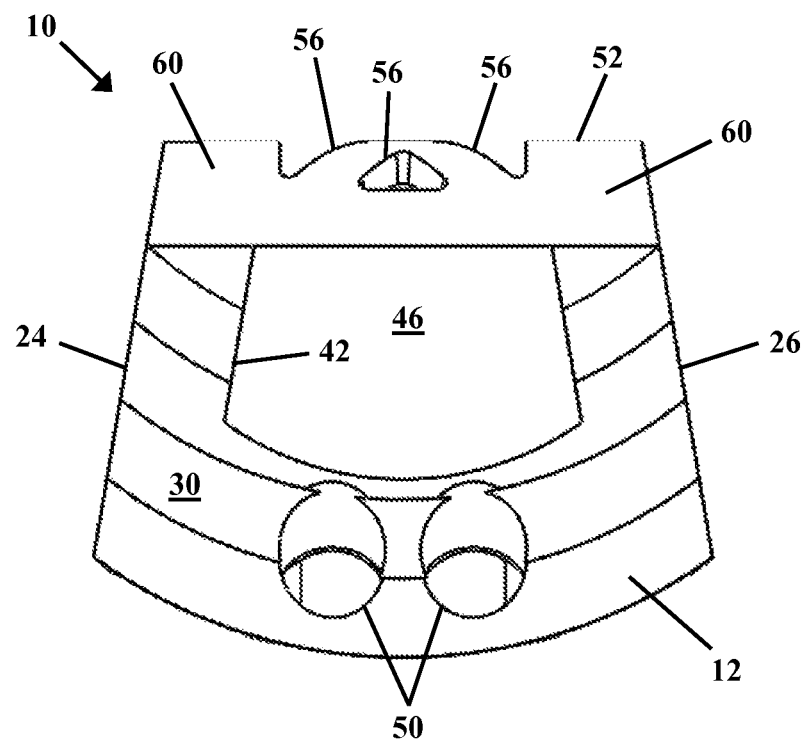
FIG. 7 is a superior view of a first exemplary embodiment of an intervertebral cage of the present disclosure.
Figure 8:
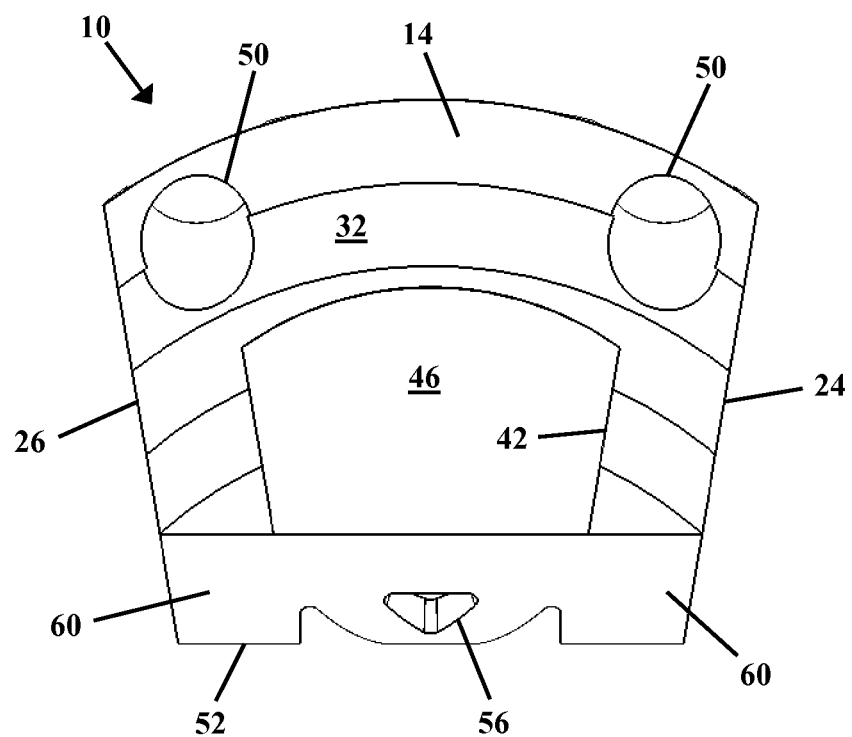
FIG. 8 is an inferior view of a first exemplary embodiment of an intervertebral cage of the present disclosure.
Figure 9:
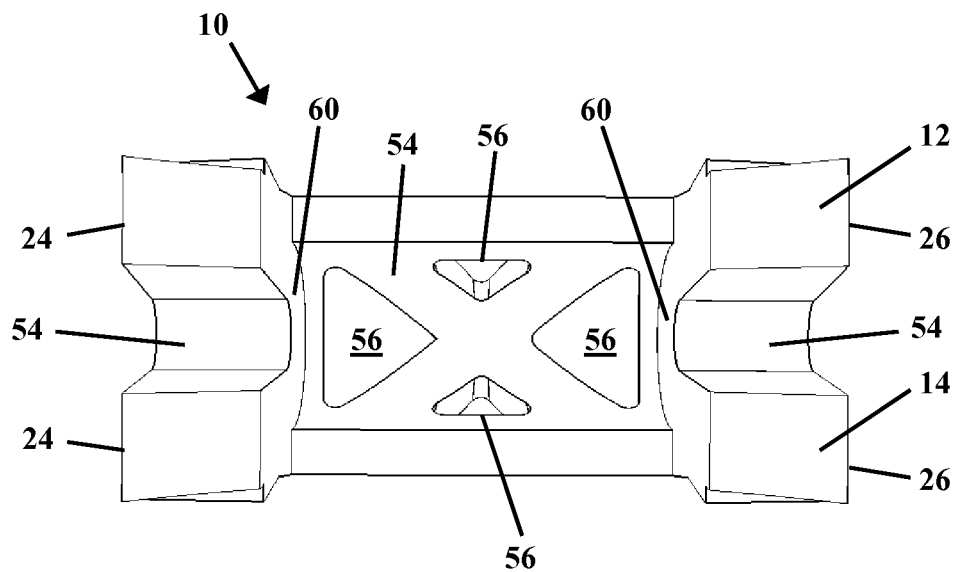
FIG. 9 is an anterior cross-section view of the first exemplary intervertebral cage of the present disclosure.
Figure 10:
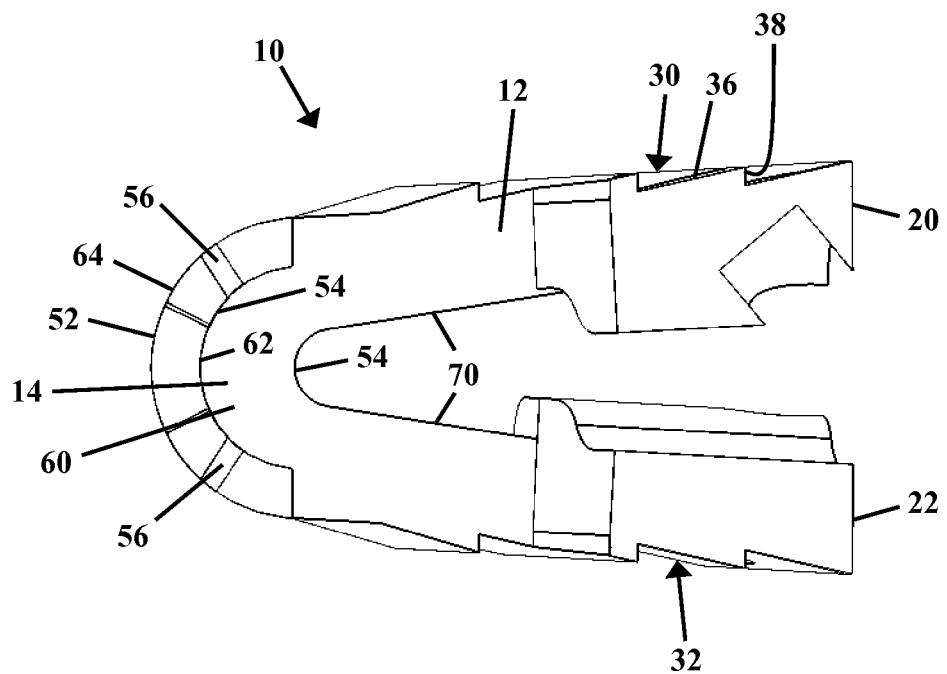
FIG. 10 is a medial cross-sectional view of the first exemplary intervertebral cage of the present disclosure.

In some embodiments, the superior member 12 and the inferior member 14 may extend in a posterior-to-anterior direction from the posterior member 16 for substantially the same distance. In some embodiments, the second free ends 20, 22 of the superior member 12 and the inferior member 14 may be substantially aligned in a superior-inferior direction as shown in FIGS. 1, 7 and 8 (e.g., in a neutral state or unloaded condition). In some embodiments, the free second ends 20, 22 of the superior member 12 and the inferior member 14 may be substantially linear or planar in the medial-lateral direction, or may define a non-linear shape, pattern or the like in the medial-lateral direction. In other embodiments, as shown in FIGS. 1, 7 and 8, the free second ends 20, 22 of the superior member 12 and the inferior member 14 may be substantially arcuate or radiused. In some such embodiments, as shown in FIGS. 1, 7 and 8, the free second ends 20, 22 of the superior member 12 and the inferior member 14 may be substantially convex such that the convexity extends in a posterior-to-anterior direction.

As shown in FIGS. 1-12, the cage 10 may be extended along a medial-lateral direction. For example, the superior member 12, the inferior member 14, and the posterior member 16 may be extended along the medial-lateral direction between opposing lateral ends or sides 24, 26 thereof. In some embodiments, the superior member 12 and the inferior member 14 may extend substantially parallel to each other in the medial-lateral direction (and spaced in the superior-inferior direction). In some embodiments, as shown in FIGS. 1-12, the superior member 12 and the inferior member 14 may extend between the lateral ends or sides 24, 26 thereof in a medial-lateral direction for the same distance along the posterior-anterior direction. In some embodiments, the lateral ends 24, 26 of the superior member 12 and the inferior member 14 of each lateral side of the cage 10 may be substantially aligned in superior-inferior direction as shown in FIGS. 1, 7 and 8 (e.g., in a neutral state or unloaded condition). In some embodiments, the lateral ends 24, 26 of the superior member 12 and the inferior member 14 may extend substantially linear or planar in the posterior-anterior direction, as shown in FIGS. 1, 7 and 8. In some other embodiments, the lateral ends 24, 26 of the superior member 12 and the inferior member 14 may define a non-linear shape, pattern or the like in the posterior-anterior direction. In some other embodiments, the lateral sides 24, 26 of the posterior member 16 may be aligned in the medial-lateral direction with the corresponding lateral sides 24, 26 of the superior member 12 and the inferior member 14, and may extend substantially parallel to the corresponding lateral sides 24, 26 of the superior member 12 and the inferior member 14, as shown in FIGS. 1-12.

In the exemplary embodiment shown in FIGS. 1-12, the opposing lateral sides 24, 26 of the cage 10, formed by the corresponding opposing lateral sides 24, 26 of the posterior member 16, superior member 12 and inferior member 14, may extend linearly (or planar) in the posterior-anterior direction (see FIGS. 7 and 8). As also shown in FIGS. 7 and 8, the opposing lateral sides 24, 26 of the cage 10 may also extend along the medial-lateral direction. In some embodiments, the medal-lateral width of the cage 10 at the posterior side or portion may be less than the medal-lateral width of the cage 10 at the anterior side or portion (e.g., at the free ends 20, 22 of the superior and inferior member 12, 14s). For example, as shown in FIGS. 7 and 8, in some embodiments the opposing lateral sides 24, 26 of the cage 10 (e.g., formed by the corresponding opposing lateral sides 24, 26 of the posterior member 16, superior member 12 and inferior member 14) may diverge in the medial-lateral direction (i.e., laterally) as they extend in the posterior-to-anterior direction. In some embodiments, as shown in FIGS. 7 and 8, the opposing lateral sides 24, 26 of the cage 10 (e.g., the opposing lateral sides 24, 26 of the posterior member 16, superior member 12 and inferior member 14) may diverge in the medial-lateral direction (i.e., laterally) as they extend in the posterior-to-anterior direction at an angle within the range of about 0 degrees to about 40 degrees, or within the range of about 10 degrees to about 25 degrees. In the exemplary illustrated embodiments, the lateral sides 24, 26 or edges in the medial-lateral direction of the cage 10 (i.e., the posterior member 16, superior member 12 and inferior member 14) substantially linearly diverge as they extend in the posterior-to-anterior direction at an angle of about 20 degrees, as shown in FIGS. 7 and 8.

Figure 3:
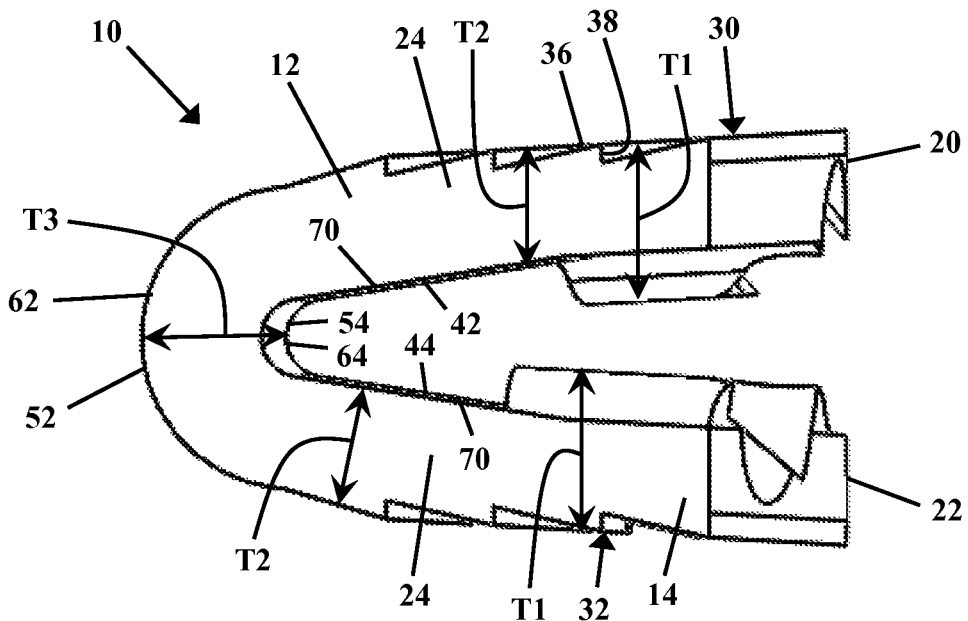
FIG. 3 is a right side view of the first exemplary intervertebral cage of the present disclosure.
Figure 4:
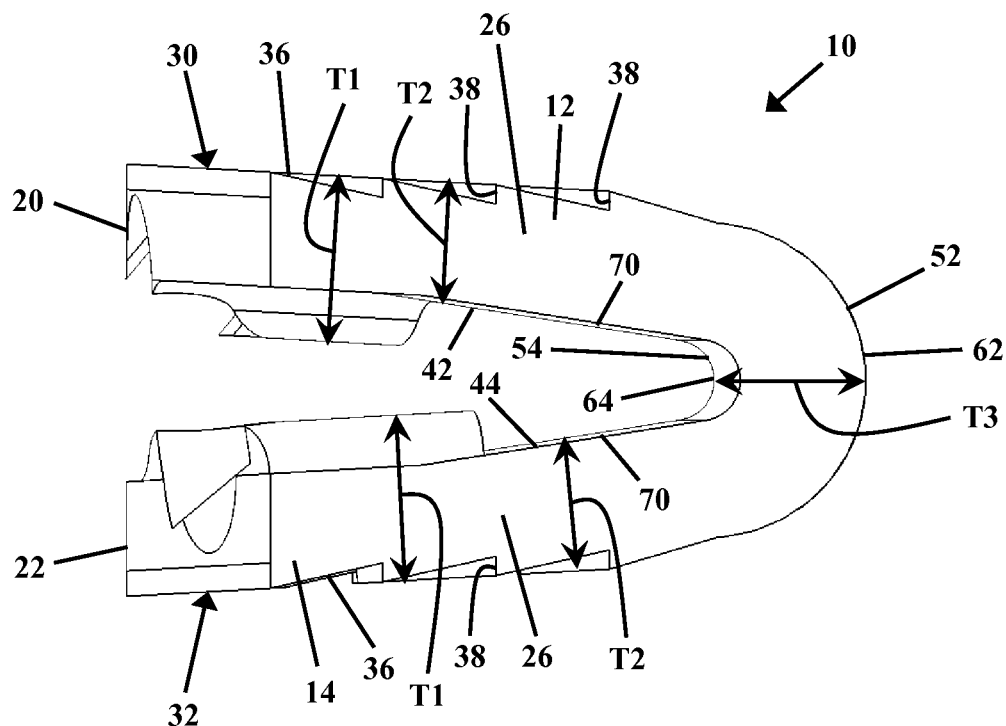
FIG. 4 is a left side view of the first exemplary intervertebral cage of the present disclosure.

As shown in FIGS. 1-6 and 9-12, the lateral sides 24, 26 of the superior member 12 and inferior member 14 of each side lateral side 24, 26 of the cage 10 may be spaced in the superior-inferior direction and are void of a connection member in the medial-lateral direction other than the posterior member 16. In this way, the cage 10 may define open lateral sides 24, 26 or ends in the medial-lateral direction between interior surfaces of the superior member 12 and inferior member 14 in the superior-inferior direction. In some embodiments, the open lateral ends 24, 26 of the cage 10 may allow for medial-lateral access, both visually and physically, into the interior of the cage 10 between the superior member 12 and the inferior member 14. In some embodiments, when viewed in the medial lateral direction as shown in FIGS. 3 and 4, the superior member 12, inferior member 14 and posterior member 16 of the cage 10 form a "U" or "V" (with the "U" or "V" laying on a side).

Figure 11:
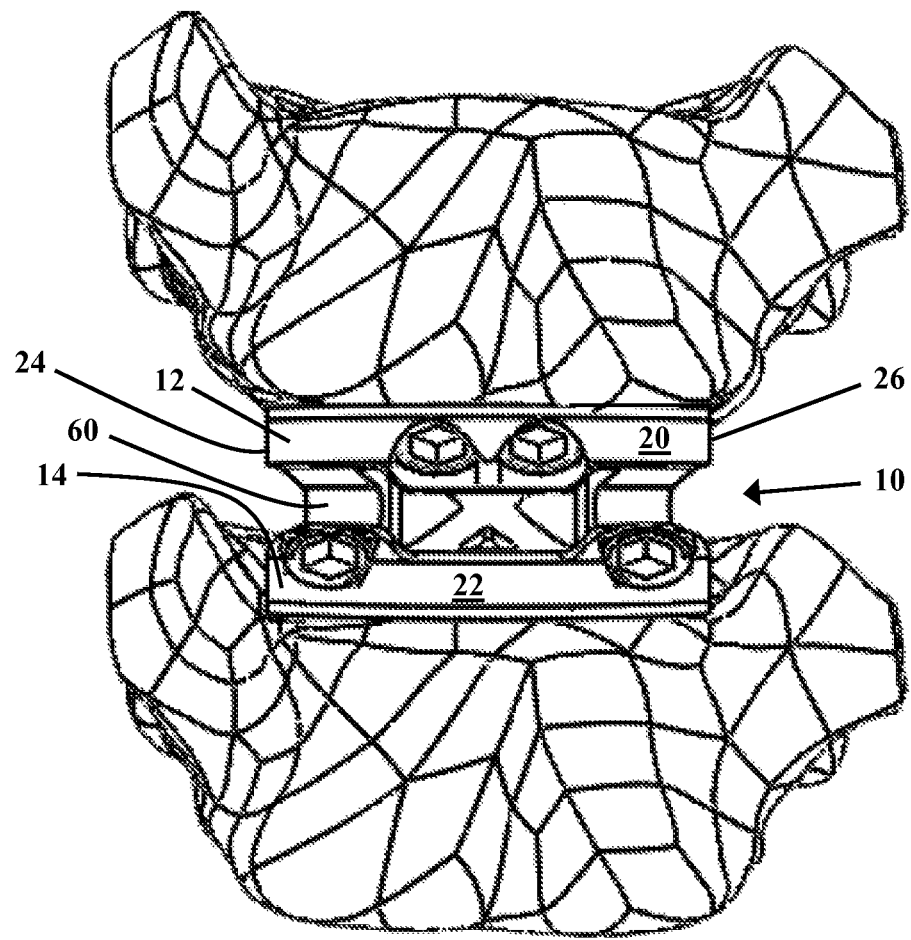
FIG. 11 is an elevational anterior perspective view of the first exemplary intervertebral cage of the present disclosure between two vertebral bodies.
Figure 12:
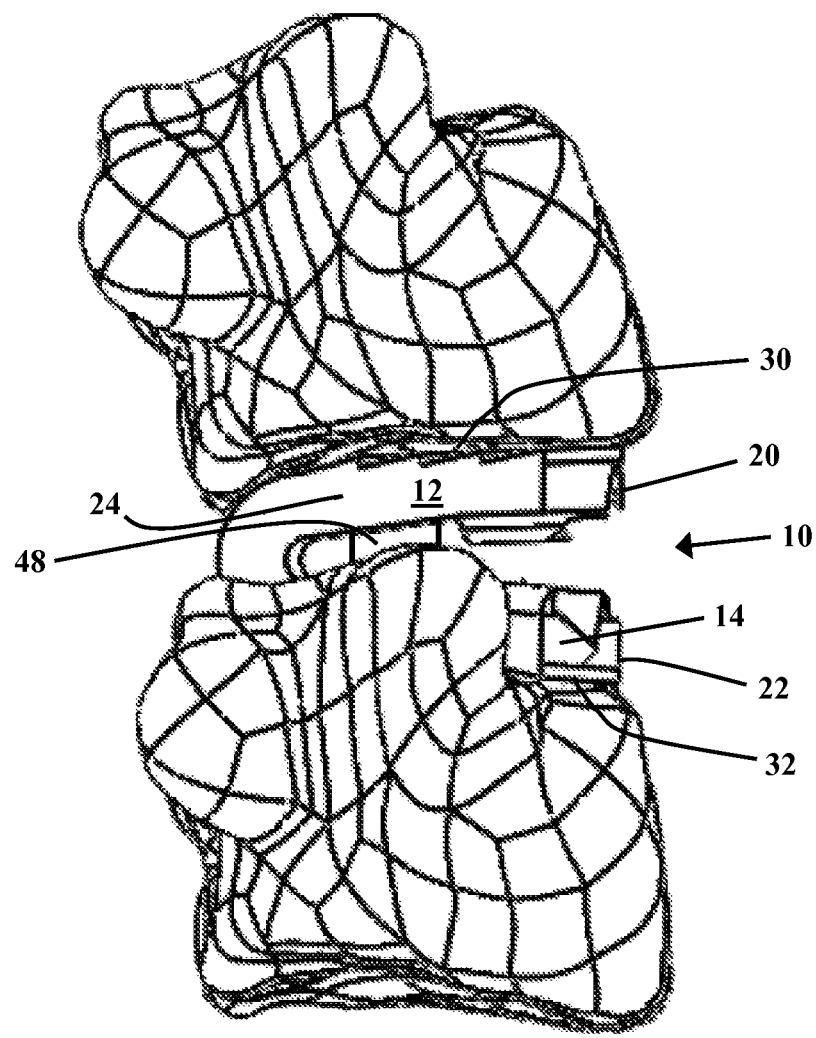
FIG. 12 is an elevational lateral perspective view of the first exemplary intervertebral cage of the present disclosure between two vertebral bodies.

In some embodiments, the superior member 12 may include an exterior first engagement surface, portion, aspect or the like 30 and the inferior member 14 may include an exterior second engagement surface 32 portion, aspect or the like 32. As shown in FIGS. 1-12, in some embodiments the first engagement surface 30 of the superior member 12 may substantially face superiorly in the inferior-superior direction, and the second engagement surface 32 of the inferior member 14 may substantially face inferiorly in the inferior-superior direction. In this way, the first engagement surface 30 of the superior member 12 and the second engagement surface 32 of the inferior member 14 may be substantially opposing surfaces in the superior-inferior direction. In some embodiments, the engagement surface 30 of the superior member 12 may engage or abut a substantially inferiorly-facing surface or aspect of a superior or first vertebral body 34, such as an end plate or a prepared (e.g., resected) portion of the first vertebral body 34, when implanted or in use, as shown in FIGS. 11 and 12. As also shown in FIGS. 11 and 12, in some embodiments the engagement surface 34 of the inferior member 14 may engage or abut a substantially superiorly-facing surface or aspect of an inferior or second vertebral body 35, such as an end plate or a prepared (e.g., resected) portion of a second vertebral body 35, when implanted or in use.

In some embodiments, the first engagement surface 30 of the superior member 12 and the second engagement surface 32 of the inferior member 14 may be substantially planar surfaces. In other embodiments, such as shown in the illustrated embodiment of FIGS. 1-12, at least one of the first and second engagement surfaces 30, 32 may include or define a surface texture, pattern or the like such that they are non-planar. However, as also shown in FIGS. 1-12, whether planar or including a surface pattern, the first and second engagement surfaces 30, 32 of the superior and inferior member 12, 14, respectively, may substantially diverge in the superior-inferior direction as they extend in the posterior-to-anterior direction from the posterior member 16 to the free second ends 20, 22 thereof. In some embodiments, the first engagement surface 30 of the superior member 12 and the second engagement surface 32 of the inferior member 14 may substantially diverge in the superior-inferior direction as they extend in the posterior-to-anterior direction from the posterior member 16 to the free second ends 20, 22 thereof at an angle less than about 10 degrees, or less than about 8 degrees. In the illustrated embodiment, the first engagement surface 30 of the superior member 12 and the second engagement surface 32 of the inferior member 14 generally diverge in the superior-inferior direction as they extend in the posterior-to-anterior direction from the posterior member 16 to the free second ends 20, 22 thereof at an angle within the range of 5 degree to about 7 degrees, such as about 6.5 degrees. In alternative embodiments (not shown), the first and second engagement surfaces 30, 32 of the superior and inferior member 12, 14, respectively, may extend substantially parallel to each other in the superior-inferior direction along a posterior-to-anterior direction from the posterior member 16 to the free second ends 20, 22 thereof.

As shown in FIGS. 1-12, the first and second engagement surfaces 30, 32 may include a ridge or surface pattern, or other pattern or texture, such that the first and second engagement surfaces 30, 32 are uneven (or non-planar) in the superior-inferior direction. In some embodiments, the pattern or texture of the first and second engagement surfaces 30, 32 may extend from the posterior member 16 to the respective free end in the posterior-anterior direction, and from the opposing lateral sides 24, 26, edge of ends thereof. In some embodiments, the entirety of the first and second engagement surfaces 30, 32 may include or define a surface pattern or texture, and in other embodiments only a portion of the first and second engagement surfaces 30, 32 may include or define a surface pattern or texture.

In some embodiments the first and second engagement surfaces 30, 32 of the cage 10 may include a ridge pattern including a plurality of ridge portions 36 and relief portions 38, as shown in FIGS. 1-12. As shown in FIGS. 1-4, in some embodiments the ridge portions 36 of the ridge pattern of the superior member 12 may extend in the posterior-to-anterior direction, along the medial-lateral direction, and in the inferior-to-superior direction in the posterior-to-anterior direction. As also shown in FIGS. 1-4, in some embodiments the ridge portions 36 of the ridge pattern of the inferior member 14 may extend in the posterior-to-anterior direction, along the medial-lateral direction, and in the superior-to-inferior direction in the posterior-to-anterior direction. In some embodiments, the ridge portions 36 of at least one of the first and second engagement surfaces 30, 32 may be arcuate along the medial-lateral direction such that they are convex along the posterior-anterior direction with the convexity extending in the posterior-to-anterior direction (e.g., a medial portion of the each ridge portion in the medial-lateral direction may be positioned further anterior than lateral portions thereof). In other embodiments, the ridge portions 36 of at least one of the first and second engagement surfaces 30, 32 of the ridge pattern may extend substantially linearly in the anterior-to-posterior direction.

In some embodiments, the relief portions 38 of the ridge pattern of the superior member 12 may extend at least in the superior-to-inferior direction between adjacent ridge portions 36, 36, as shown in FIGS. 1-4. The relief portions 38 of the ridge pattern of the superior member 12 may also extend along the medial-lateral direction, such as substantially parallel to the ridge portions 36 of the ridge pattern, as shown in FIGS. 1-4. In some embodiments, the relief portions 38 of the ridge pattern of the superior member 12 extend in the superior-to-inferior direction and along the posterior-anterior direction between adjacent ridge portions 36. In some embodiments, the relief portions 38 of the ridge pattern of the inferior member 14 may extend at least in the inferior-to-superior direction between adjacent ridge portions 36, as shown in FIGS. 1-4. The relief portions 38 of the ridge pattern of the inferior member 14 may also extend along the medial-lateral direction, such as substantially parallel to the ridge portions 36 of the ridge pattern, as shown in FIGS. 1-4. In some embodiments, the relief portions 38 of the ridge pattern of the inferior member 14 extend in the inferior-to-superior direction and along the posterior-anterior direction between adjacent ridge portions 36.

As shown in FIGS. 1-4, the first engagement surface 30 of the superior member 12 may include a first ridge pattern that may be arranged or configured such that a first ridge portion 36 of the first engagement surface 30 of the superior member 12 that is adjacent and posterior to a second ridge portion 36 in the posterior-anterior direction is at least partially positioned superior to the second ridge portion. For example, the first ridge portion 36 may extend in inferior-to-superior direction along the posterior-to-anterior direction, and an adjoining relief portion may extend from the further anterior and superior end of the first ridge portion to form a first tip therebetween. The adjoining relief portion may extend in a superior-to-inferior direction to the second ridge portion. The second ridge portion may also extend in an inferior-to-superior direction along the posterior-to-anterior direction, and may extend to a second tip positioned further superior than the first tip of the first portion. In this way, the first engagement surface 30 of the superior member 12 may extend generally or substantially in the inferior-to-superior direction, but include portions (e.g., the relief portions 38) that extend in an inferior-to-superior direction along the posterior-to-anterior direction. Such a tooth or stair like pattern of the first engagement surface 30 of the superior member 12 may act to prevent the cage 10 from translating in the posterior-to-anterior direction (or "backing out") when implanted and in engagement with a superior vertebral body 34.

Similarly, as shown in FIGS. 1-4, the second engagement surface 32 of the inferior member 14 may include a second ridge pattern that may be arranged or configured such that a first ridge portion 36 of the second engagement surface 32 of the superior member 12 that is adjacent and posterior to a second ridge portion 36 in the posterior-anterior direction is at least partially positioned inferior to the second ridge portion. For example, the first ridge portion 36 may extend in superior-to-inferior direction along the posterior-to-anterior direction, and an adjoining relief portion 38 may extend from the further anterior and inferior end of the first ridge portion to form a first tip therebetween. The adjoining relief portion 38 may extend in an inferior-to-superior direction to the second ridge portion. The second ridge portion may also extend in the superior-to-inferior direction along the posterior-to-anterior direction, and may extend to a second tip positioned further inferior than the first tip of the first portion. In this way, the second engagement surface 32 of the inferior member 14 may extend generally or substantially in the superior-to-inferior direction, but include portions (e.g., the relief portions 38) that extend in an inferior-to-superior direction along the posterior-to-anterior direction. Such a tooth or stair like pattern of the second engagement surface 32 of the inferior member 14 may act to prevent the cage 10 from translating (or "backing out") when implanted and in engagement with an inferior vertebral body 35.

In some embodiments, the superior member 12 and the inferior member 14 may each include at least one first aperture 40 extending through the members 12, 14 in the superior-inferior direction, as shown in FIGS. 1-12. For example, the at least one first aperture 40 of the superior member 12 may extend from the first engagement surface 30 to a first interior surface 42 opposing the first engagement surface 30 in the superior-inferior direction. Similarly, the at least one first aperture 40 of the inferior member 14 may extend from the second engagement surface 32 to the second interior surface 44 opposing the second engagement surface 32 in the superior-inferior direction. In some embodiments, the at least one first apertures 40 of the superior and/or inferior members 12, 14 may be positioned in medial portion of the members 12, 14 in medial-lateral and posterior-anterior directions.

In some embodiments, the at least one first aperture 40 extending through the superior and inferior members 12, 14 in the superior-inferior direction may at least partially overlap in the superior-inferior direction. Stated differently, the at least one first aperture 40 extending through the superior and inferior members 12, 14 in the superior-inferior direction may at least partially overlap in the medial-lateral and posterior-anterior directions (but spaced in the superior-inferior direction) such that they are at least partially aligned along a superior-inferior direction extending parallel to the frontal and/or sagittal planes (and/or perpendicular to the transverse plane). In some embodiments, as shown in FIGS. 1-12, the at least one first apertures 40 of the members 12, 14 define the same shape and size, and are aligned, in the medial-lateral and anterior-posterior directions such that they are aligned along a superior-inferior direction extending parallel to the frontal and/or sagittal planes (and/or perpendicular to the transverse plane) (see FIGS. 7 and 8).

In some embodiments, as shown in FIGS. 1-12, the at least one first apertures 40 of the superior member 12 and the inferior member 14 at least partially define a first pathway 46 through the intervertebral cage 10 in the superior-inferior direction. In some embodiments, the cage 10 is substantially hollow or substantially void of structure between the at least one first aperture 40 of the superior and inferior members 12, 14 such that the at least one first apertures 40 of the superior member 12 and the inferior member 14 define the first pathway 46 through the intervertebral cage 10 in the superior-inferior direction. In some embodiments, the first pathway 46 extends through the intervertebral cage 10 in the superior-inferior direction between the first engagement surface 30 of the superior member 12 and the second engagement surface 32 of the inferior member 14. In some in situ embodiments, the first pathway 46 extends through the intervertebral cage 10 in the superior-inferior direction between a superior vertebral body 34 adjacent the first engagement surface 30 of the superior member 12 and an inferior vertebral body 35 adjacent the second engagement surface 32 of the inferior member 14, as shown in FIGS. 11 and 12. In some embodiments, bone graft material 48 may be positioned within the first pathway 46 of the intervertebral cage 10 between the superior and inferior members 12, 14, as shown in FIG. 12. For example, such bone graft material 48 may be translated through the anterior opening of the intervertebral cage 10 between the superior and inferior members 12, 14 and into the first pathway 46 (either before or after the cage 10 is implanted).

In some embodiments, the at least one first aperture 40 of the superior and inferior members 12, 14, and/or the first pathway 46, may include or define a surface area along the transverse plane of at least about 15% of the surface area of at least one of the first engagement surface 30 and the second engagement surface 32. In some such embodiments, the at least one first aperture 40 of the superior and inferior members 12, 14, and/or the first pathway 46, may include or define a surface area along the transverse plane within the range of about 15% to about 50% of the surface area of at least one of the first engagement surface 30 and the second engagement surface 32. In some such embodiments, the at least one first aperture 40 of the superior and inferior members 12, 14, and/or the first pathway 46, may include or define a surface area along the transverse plane within the range of about 25% to about 40% of the surface area of at least one of the first engagement surface 30 and the second engagement surface 32. In some such embodiments, the at least one first aperture 40 of the superior and inferior members 12, 14, and/or the first pathway 46, may include or define a surface area along the transverse plane within the range of about 25% to about 30% of the surface area of at least one of the first engagement surface 30 and the second engagement surface 32.

In some embodiments, the at least one first aperture 40 of the superior and inferior members 12, 14, and/or the first pathway 46, may include or define a surface area along the transverse plane of at least about 30 square millimeters. In some embodiments, the at least one first aperture 40 of the superior and inferior members 12, 14, and/or the first pathway 46, may include or define a surface area along the transverse plane within the range of about 30 square millimeters and about 100 square millimeters. Some such cage 10 embodiments may be particularly advantageous for use with cervical vertebral bodies 34, 35. In some embodiments, the at least one first aperture 40 of the superior and inferior members 12, 14, and/or the first pathway 46, may include or define a surface area along the transverse plane of at least about 50 square millimeters. In some embodiments, the at least one first aperture 40 of the superior and inferior members 12, 14, and/or the first pathway 46, may include or define a surface area along the transverse plane within the range of about 50 square millimeters and about 300 square millimeters. Some such cage 10 embodiments may be particularly advantageous for use with lumbar vertebral bodies 34, 35.

With reference to FIGS. 1-4, in some embodiments the cage 10 may include one or more second aperture 50 extending through at least one of the superior and inferior members 12, 14 at least generally in the superior-inferior member 14. In some embodiments, the at least one second aperture 50 may be utilized to secure, couple, fix or the like the cage 10 to the superior and inferior vertebral bodies 34, 35. For example, a bone fixation device, such as a bone screw, pin or other member may pass through the at least one second aperture 50 and into an adjacent vertebral body 34, 35 at least generally in the superior-inferior direction. The superior and inferior members 12, 14 may include any number or arrangement of second apertures 50 extending therethrough at least generally in the superior-inferior direction. In some embodiments, the at least one second aperture 50 may be positioned or configured such that it may be accessed after the cage 10 is implanted between superior and inferior vertebral bodies 34, 35. For example, in some embodiments, as shown in FIGS. 1-12 the superior member 12 and/or the inferior member 14 may include at least one second aperture 50 extending therethrough in a superior-inferior direction that is positioned proximate the second free ends 20, 22 of the members 12, 14. In this way, the at least one second aperture 50 may be accessed from the open anterior end of the cage 10 between the superior and inferior members 12, 14 while the cage 10 is implanted.

Figure 5:
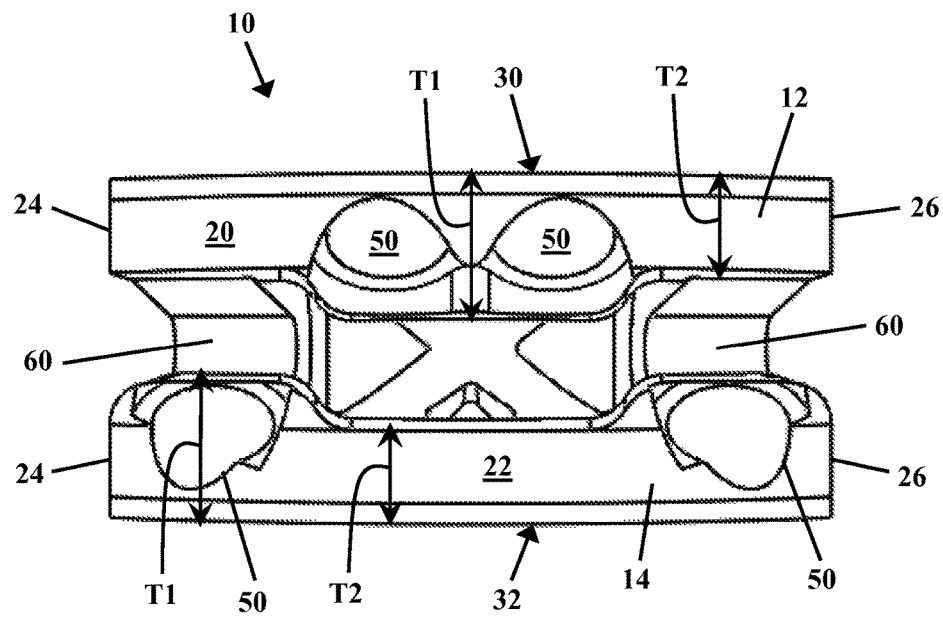
FIG. 5 is an anterior view of the first exemplary intervertebral cage of the present disclosure.
Figure 6:
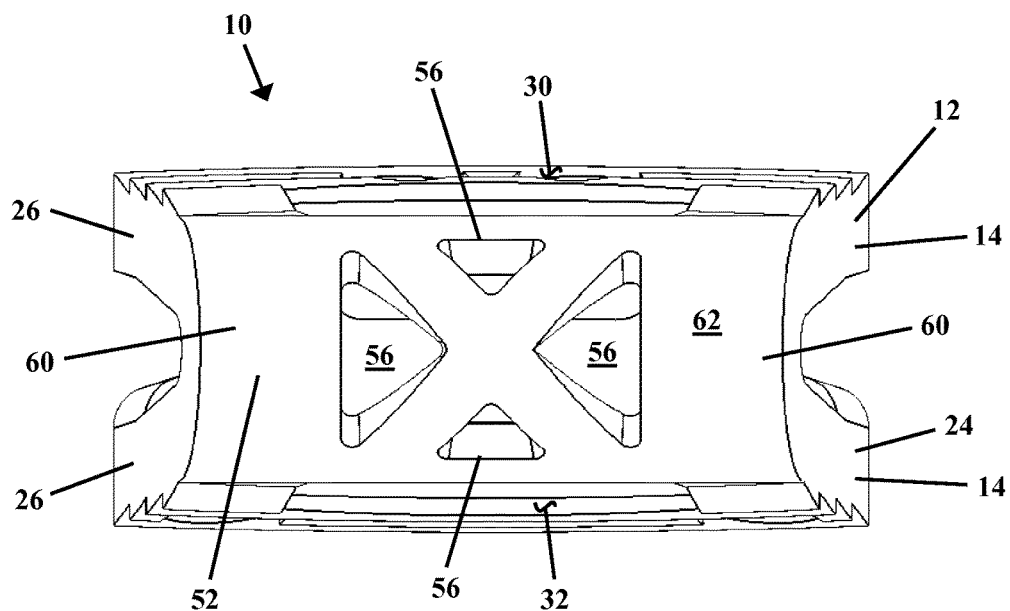
FIG. 6 is a posterior view of the first exemplary intervertebral cage of the present disclosure.

In some embodiments, each of the superior member 12 and the inferior member 14 define a thickness between the first and second engagement surfaces 30, 32 and substantially opposing interior surfaces 20, 22 opposing the engagement surfaces. In some embodiments, first and second interior surfaces 42, 44 substantially oppose the first and second engagement surfaces 30, 32, such as in the superior-inferior direction. In some embodiments, the thicknesses of the superior member 12 and the inferior member 14 extend at least generally in the superior-inferior direction. In some exemplary embodiments, as shown in FIGS. 3-5, the superior member 12 and the inferior member 14 each include at least one second aperture 50 proximate the second free end 20, 22 thereof, and the superior member 12 and the inferior member 14 define a first thickness T1 extending at least partially about the at least one second aperture 50, and a second thickness T2 that is less than the first thickness T1 spaced from the at least one second aperture 50.

In some embodiments, the interior surface 42 of the superior member 12 may extend further in the superior-to-inferior direction about the at least one second aperture 50 formed therethrough than areas or portions spaced from the at least one second aperture 50, as shown in FIGS. 1, 3-5 and 11. As also shown in FIGS. 1, 3-5 and 11, in some embodiments the interior surface 44 of the inferior member 14 may extend further in the inferior-to-superior direction about the at least one second aperture 50 formed therethrough than areas or portions spaced from the at least one second aperture 50. In this way, the cage 10 may include an extended thickness, portion, ridge, bump or raised portion on the interior surface 42, 44 about the at least one aperture of the superior member 12 and/or inferior member 14.

In some embodiments that include an extend thickness on the interior surfaces 20, 22 of the superior and inferior members 12, 14 about at least one second aperture 50 formed therethrough, the second apertures 50 and corresponding extended thickness regions about the interior surface 20, 22 thereof of the superior member 12 and the inferior member 14 are offset or spaced from one another along the medial-lateral direction from each other. In this way, in some embodiments a second aperture 50 and corresponding interior extended portion of each of the superior and inferior members 12, 14 are not aligned in the medial-lateral (and thereby not aligned along the superior-inferior direction) with may limit compression/extension of the superior and inferior members 12, 14 with respect to one another along the superior-inferior direction. In some embodiments, the at least one second apertures 50 and corresponding interior extended regions of the superior and inferior members 12, 14 may be substantially aligned along the posterior-anterior direction proximate the free second ends 20, 22 thereof, and spaced along the medial-lateral and superior-inferior directions.

As shown in FIGS. 1-12, in some embodiments each of the superior and inferior members 12, 14 may include at least two second apertures 50 proximate the second free ends 20, 22 thereof and extending therethrough in the superior-inferior direction. As also shown in FIGS. 1-12, in some embodiments the superior member 12 or inferior member 14 may include a pair of the second apertures 50 positioned in a medial portion of the respective member 12, 14 along the medial-lateral direction, and the other of the superior member 12 or inferior member 14 may include a pair of second apertures 50 each positioned in lateral portions of the respective member along the medial-lateral direction. In some embodiments, the second apertures 50 positioned in lateral portions in the medial-lateral direction of the superior member 12 or inferior member 14 may be proximate the junction of the respective lateral side 24, 26 and second free end 20, 22 of the respective member 12, 14.

In some embodiments, at least one second aperture 50 of the superior member 12 may extend through the superior member 12 from the interior surface 42 to the first engagement surface 30 in generally a superior-inferior direction. For example, in some embodiments the at least one second aperture 50 of the superior member 12 may extend through the superior member 12 in the superior-inferior direction at an angle in the anterior-posterior direction from the transverse plane. In some such embodiments, the at least one second aperture 50 of the superior member 12 may extend through the superior member 12 in the superior-inferior direction at an angle in the anterior-to-posterior direction from the transverse plane as it extends in the inferior-to-superior direction through the superior member 12 within the range of about 10 degrees to about 50 degrees. In the exemplary embodiment shown in FIGS. 1-12, the two second apertures 50 of the superior member 12 extend through the superior member 12 in the superior-inferior direction at an angle in the anterior-to-posterior direction from the transverse plane of about 40 degrees as they extend in the inferior-to-superior direction through the superior member 12.

In some embodiments, at least one second aperture 50 of the inferior member 14 may extend through the inferior member 14 from the interior surface 44 to the second engagement surface 32 in generally a superior-inferior direction. For example, in some embodiments the at least one second aperture 50 of the inferior member 14 may extend through the inferior member 14 in the superior-inferior direction at an angle in the anterior-posterior direction from the transverse plane. In some such embodiments, the at least one second aperture 50 of the inferior member 14 may extend through the inferior member 14 in the superior-inferior direction at an angle in the anterior-to-posterior direction from the transverse plane as it extends in the superior-to-inferior direction through the superior member 12 within the range of about 10 degrees to about 50 degrees. In the exemplary embodiment shown in FIGS. 1-12, the two second apertures 50 of the superior member 12 extend through the superior member 12 in the superior-inferior direction at an angle in the anterior-to-posterior direction from the transverse plane of about 40 degrees as they extend in the inferior-to-superior direction through the superior member 12.

In some embodiments, the at least one second aperture 50 of the superior member 12 and/or inferior member 14 may be angled along the medial-lateral direction at it extends through the members 12, 14 in the superior-inferior direction from the interior surfaces 20, 22 to the engagement surfaces 30, 32 thereof. In some embodiments, the at least one second aperture 50 of the superior member 12 and/or inferior member 14 may be angled along the medial-lateral direction with respect to the midsagittal plane at it extends through the members 12, 14 less than about 30 degrees. In the exemplary embodiment shown in FIGS. 1-12, the two second apertures 50 of the superior member 12 and/or inferior member 14 are angled at about 5 degrees along the medial-lateral direction with respect to the midsagittal plane at they extend through the members 12, 14. In some other embodiments, the at least one second aperture 50 of the superior member 12 and/or inferior member 14 may not be angled along the medial-lateral direction at it extends through the members 12, 14 in the superior-inferior direction from the interior surfaces 20, 22 to the engagement surfaces thereof 30, 32 (e.g., parallel to the midsagittal plane).

In some embodiments, the at least one second aperture 50 of the superior member 12 and/or inferior member 14 may be angled in the lateral-to-medial direction with respect to the midsagittal plane at it extends through the members 12, 14 from the interior surface 42, 44 to the engagement surface 30, 32 thereof. For example, the at least one second aperture 50 of the superior member 12 and/or inferior member 14 may be angled in the lateral-to-medial direction with respect to the midsagittal plane at it extends through the members 12, 14 from the interior surface 42, 44 to the engagement surface 30, 32 thereof when the at least one second aperture 50 is positioned in a lateral portion of the members, such as proximate one of lateral sides 24, 26 of the members 12, 14 as shown in the exemplary inferior member 14 of FIGS. 1-12. In some such embodiments, the second apertures 50 (and a member extending therethrough, such as a bone fixation device (e.g., a bone screw)) may converge in the medial lateral direction as they extend through the members 12, 14 from the interior surface 40, 42 to the engagement surface 30, 32 thereof. As another example, the at least one second aperture 50 of the superior member 12 and/or inferior member 14 may be angled in the medial-to-lateral direction with respect to the midsagittal plane as it extends through the members 12, 14 from the interior surface 40, 42 to the engagement surface 30, 32 thereof when the at least one second aperture 50 is positioned in a medial portion of the members 12, 14 as shown in the exemplary superior member 12 of FIGS. 1-12. In some such embodiments, two of the at least one second aperture 50 may converge in the medial lateral direction as they extend through the members 12, 14 from the interior surface 42, 44 to the engagement surface 30, 32 thereof. In such embodiments, the second apertures 50 (and a member extending therethrough, such as a bone fixation device (e.g., a bone fixation device)) may diverge in the medial lateral direction as they extend through the members 12, 14 from the interior surface 42, 44 to the engagement 30, 32 surface thereof.

As shown in FIGS. 1-12, in some embodiments the posterior member 16 may extend substantially linearly in the medial-lateral direction, and include an exterior substantially posterior-facing surface 52 and an interior substantially anterior-facing surface 54. In some embodiments the posterior member 16 includes at least one third aperture 36 extending through the posterior member 16 in the posterior-anterior direction. In some such embodiments, the at least one third aperture 36 may be positioned substantially medial in the medial-lateral direction and/or the superior-inferior direction of the posterior member 16. In some embodiments, the posterior member 16 may define differing thicknesses, such as along the medial-lateral direction. For example, as shown in the cross-sectional views of the exemplary embodiment in FIGS. 9 and 10, the posterior member 16 may be substantially thicker, such as in the medial lateral and/or superior-inferior directions, at the lateral end portions thereof as compared to the medial portion thereon. In some such embodiments, the posterior member 16 may include two first strut like members 60 at the lateral sides 24, 26 of the cage 10 (i.e., the lateral sides 24, 26 of the superior and inferior member 12, 14). In some embodiments, the lateral side portions 24, 26 of the posterior member 16 may be connected in the medial-lateral direction by a medial portion extending therebetween that may be thinner, such as in the anterior-posterior direction, than the lateral side portions thereof. In other embodiments, the lateral side portions of the posterior member 16 may not be connected in the medial-lateral direction, such that the posterior member 16 is formed of two independent lateral side portions or first struts 60 that extend between the superior and inferior members 12, 14 at opposing lateral sides 24, 26 (i.e., the superior and inferior members 12, 14 connect the independent lateral side portions or first struts 60).

In some embodiments, the third thickness T3 of at least the lateral side portions or first struts 60 of the posterior member 16, as shown in FIGS. 3 and 4, extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about ¼ millimeter and about 3 millimeters, or within the range of about 1 millimeter and about 3 millimeters, or about 2 and ½ millimeters. Some such cage 10 embodiments may be particularly advantageous for use with cervical vertebral bodies 34, 35. In some other embodiments, the thickness T3 of at least the lateral side portions or first struts 60 of the posterior member 16, as shown in FIGS. 3 and 4, extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 2 millimeter and about 5 millimeters, or about 4 millimeters. Some such cage 10 embodiments may be particularly advantageous for use with lumbar vertebral bodies 34, 35. It is noted that the thickness of other portions of at least the lateral side portions or first struts 60 of the posterior member 16 may define differing thicknesses as compared to the thickness T3 of at least the lateral side portions or first struts 60 extending between the furthest posterior-positioned exterior surface and the furthest anterior-positioned interior surface in the posterior-anterior direction (and/or measured along the transverse plane from the furthest posterior-positioned exterior surface) (i.e., the thickness of the posterior member 16, such as the lateral or strut portions, may vary).

As also shown in FIGS. 1-12, in some embodiments the posterior member 16 may extend non-linearly in the superior-inferior direction. For example, the posterior member 16 may extend non-linearly in the anterior-posterior direction as it extends in the superior-inferior direction. In the exemplary embodiment shown in FIGS. 1-12, the posterior member 16 is substantially convex such that the convexity extends in a posterior-to-anterior direction. For example, a medial portion of the posterior member 16 in the superior-inferior direction may be positioned posterior to the portions adjoining or adjacent the superior and inferior members 12, 14, as shown in FIGS. 3 and 4.

In some embodiments, as shown in FIGS. 1-12, the posterior member 16 (such as at least the lateral side portions or first struts 60 thereof) may extend non-linearly in the superior-inferior direction such that the posterior side or end of the cage 10 includes a substantially convex outer surface extending between the first and second engagement surfaces 30, 32 of the superior and inferior members 12, 14, respectively, and the interior side or end thereof extending between the first and second interior surfaces 42, 44 of the superior and inferior members 12, 14, respectively includes a substantially concave interior surface. In some embodiments, the substantially convex outer surface of the posterior member 16 and/or substantially concave interior surface of the posterior member 16 may include one or more radius of curvature, linear or planar segment or combination thereof. For example, in some embodiments the substantially convex outer surface of the posterior member 16 and/or substantially concave interior surface of the posterior member 16 may include a curvilinear shape with multiple radii of curvature. As another example, in some embodiments the substantially convex outer surface of the posterior member 16 and/or substantially concave interior surface of the posterior member 16 may include a curvilinear shape with multiple radii of curvature integrated with straight segments. As yet another example, in some embodiments the substantially convex outer surface of the posterior member 16 and/or substantially concave interior surface of the posterior member 16 may include multiple straight segments with radiused or chamfered ends.

As shown in FIGS. 3-4, in some embodiments the substantially convex outer surface of the posterior member 16 (such as the first strut portions thereof) may define a first radiused exterior surface 62 defined by a first radius that extends between the first and second engagement surfaces 30, 32 of the superior and inferior member 12, 14, respectively. In some embodiments, the first radius of the first radiused surface 62 of the posterior member 16 (such as the first strut portions thereof) is within the range of about 2 millimeters and 18 millimeters, or within about 2 millimeters and about 10 millimeters. As also shown in FIGS. 3-4, in some embodiments the substantially concave interior surface of the posterior member 16 (such as the first strut portions thereof) may define a second radiused interior surface 64 defined by a second radius that extends between the first and second interior surfaces 42, 44 of the superior and inferior member 12, 14, respectively. In some embodiments, as shown in FIGS. 3 and 4, the second radius of the concave interior second radiused surface 64 of the posterior member 16 (such as the first strut portions thereof) is less than the first radius of the outer first radiused surface 62. In some other embodiments, the second radius of the concave interior second radiused surface 64 of the posterior member 16 (such as the first strut portions thereof) is greater than the first radius of the outer first radiused surface 62. In some embodiments, the second radius of the concave interior second radiused surface 64 of the posterior member 16 (such as the first strut portions thereof) is within the range of about ¼ millimeter and 15 millimeters, or within about 1 millimeters and about 4 millimeters, or about 1.5 millimeters. Some such cage 10 embodiments may be particularly advantageous for use with cervical vertebral bodies 34, 35. In some other embodiments, the second radius of the concave interior second radiused surface 64 of the posterior member 16 (such as the first strut portions thereof) is within the range of about ¼ millimeter and 20 millimeters, or within about 2 millimeters and about 10 millimeters, or about 3 millimeters. Some such cage 10 embodiments may be particularly advantageous for use with lumbar vertebral bodies 34, 35.

As shown in FIGS. 3-4, in some embodiments the substantially convex outer surface of the posterior member 16 (such as the first strut portions thereof) may define a first radiused exterior surface 62 defined by a first radius and the substantially concave interior surface of the posterior member 16 (such as the first strut portions thereof) may define a second radiused interior surface 64 defined by a second radius. In some such embodiments, the axis or center of the first radius and the second radius may differ. For example, as shown in FIGS. 3 and 4, the axis or center of the first radius of the first radiused exterior surface 62 and the axis or center of the second radius of the second radiused interior surface 64 are offset or spaced along the anterior-posterior direction. For example the axis or center of the first radius of the first radiused exterior surface 62 may be positioned further anterior than the axis or center of the second radius of the second radiused interior surface 44. In such a way, the thickness of the posterior member 16 (such as the first strut portions thereof) may vary, for example.

Figure 13:
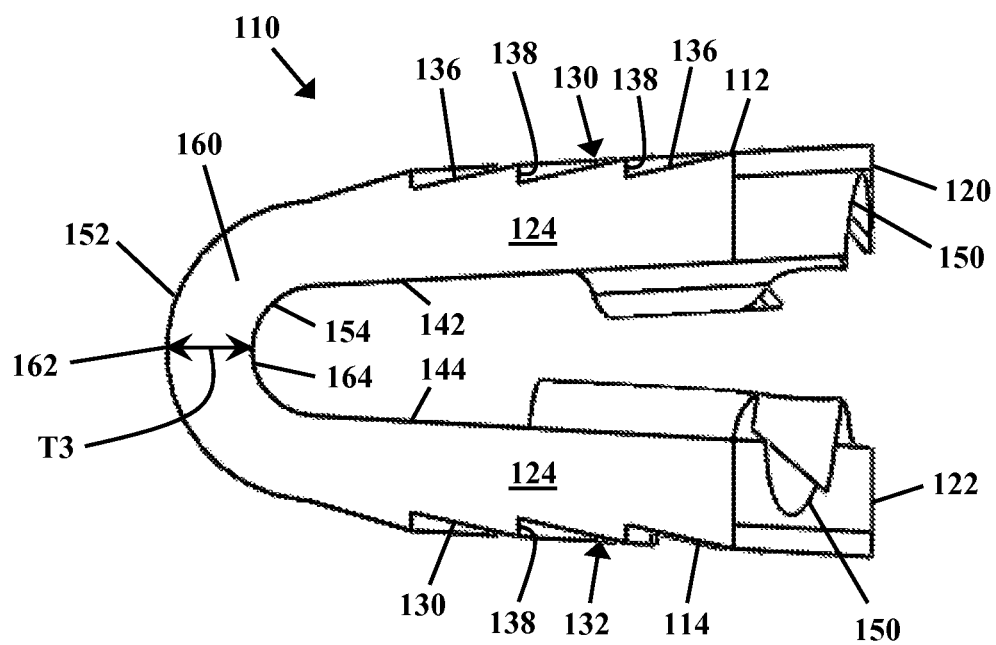
FIG. 13 is lateral view of a second exemplary intervertebral cage of the present disclosure.

An exemplary embodiment of another intervertebral cage according to the present disclosures is shown in FIG. 13 and generally indicated with the reference numeral 110. Some aspects, elements and/or functions of exemplary intervertebral cage 10 may be the same or similar in structure and/or function, at least in part, to the exemplary intervertebral cage 10 described above and shown in FIGS. 1-12, and therefore at least some like reference numerals preceded by the numeral "1" are used to indicate at least some such potential similar aspects, elements and/or functions. One difference between intervertebral cage 110 of FIG. 13 and intervertebral cage 10 of FIGS. 1-12 may be the third thickness T3 of the posterior member 116. As shown in the lateral side view of FIG. 13, the third thickness T3 of at least the lateral side portions or first struts 160 of the posterior member 116 extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 1 millimeter and about 3 millimeters, or about 1 and ¾ millimeters. Some such cage 110 embodiments may be particularly advantageous for use with cervical vertebral bodies 134, 135. In some other embodiments, as shown in FIG. 13, the thickness T3 of at least the lateral side portions or first struts 160 of the posterior member 116, extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 2 millimeter and about 5 millimeters, or about 3 millimeters. Some such cage 110 embodiments may be particularly advantageous for use with lumbar vertebral bodies 134, 135.

Another difference between intervertebral cage 110 of FIG. 13 and intervertebral cage 10 of FIGS. 1-12 may be the position of the axis or center of the first radius of the convex outer first radiused surface 162 and the axis or center of the second radius of the concave interior second radiused surface 164 of the posterior member 116 (such as the first strut portions thereof). In the exemplary intervertebral cage 110 of FIG. 13, the axis or center of the second radius and the axis or center of the first radius may be common (i.e., the same position). For example, the axis or center of the second radius and the axis of the axis or center of the first radius may be aligned in the poster-anterior direction. As such, the thickness T3 of at least the lateral side portions or first struts 160 of the posterior member 116 may be uniform about the common axis of the first radius and second radius. Stated differently, as the convex outer first radiused surface 162 and the concave interior second radiused surface 164 of the posterior member 116 (such as the first strut portions thereof) may be concentric, the thickness T3 of at least the lateral side portions or first struts 160 of the posterior member 116 may be uniform about the common axis.

Figure 14:
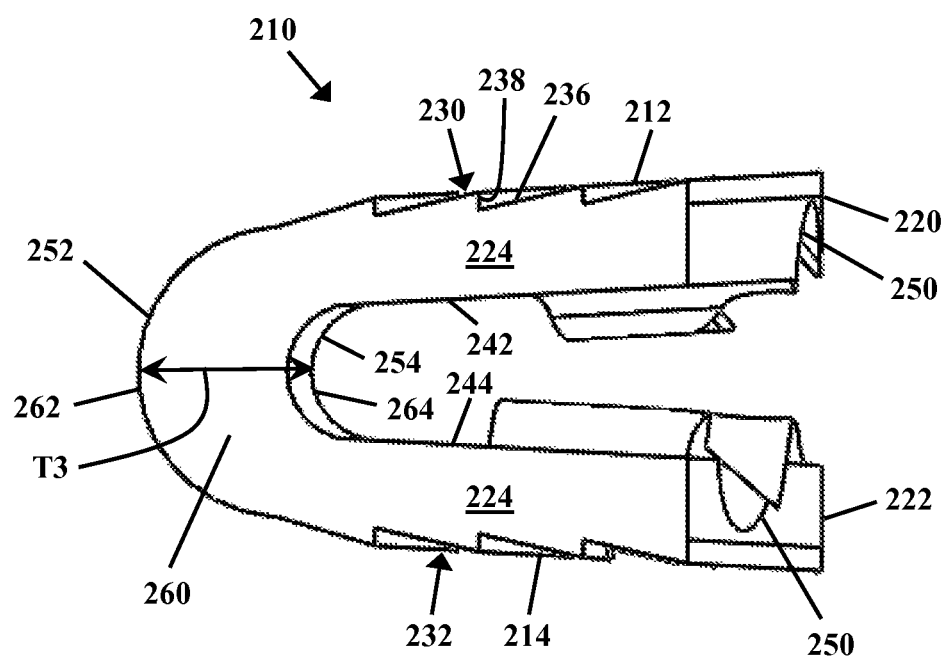
FIG. 14 is a lateral view of a third exemplary intervertebral cage of the present disclosure.

An embodiment of another intervertebral cage according to the present disclosures is shown in FIG. 14 and generally indicated with the reference numeral 210. Some aspects, elements and/or functions of intervertebral cage 210 may be the same or similar in structure and/or function, at least in part, to the exemplary intervertebral cage 10 and 110 described above, and therefore at least some like reference numerals preceded by the numeral "2" are used to indicate at least some such potential similar aspects, elements and/or functions. One difference between exemplary intervertebral cage 210 of FIG. 14 and exemplary intervertebral cage 10 and 110 may be the third thickness T3 of the posterior member 216. As shown in the lateral side view of FIG. 14, the third thickness T3 of at least the lateral side portions or first struts 260 of the posterior member 216 extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 1 millimeter and about 3 millimeters, or about 2 and ½ millimeters. Some such cage 210 embodiments may be used with cervical vertebral bodies 234, 235. In some other embodiments, as shown in FIG. 14, the thickness T3 of at least the lateral side portions or first struts 260 of the posterior member 216, extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 2 millimeter and about 6 millimeters, or about 4 millimeters. Some such cage 210 embodiments may be particularly advantageous for use with lumbar vertebral bodies 234, 235.

Another difference between intervertebral cage 210 of FIG. 14 and intervertebral cage 10 and/or 110 may be the position of the axis or center of the first radius of the convex outer first radiused surface 262 and the axis or center of the second radius of the concave interior second radiused surface 264 of the posterior member 216 (such as the first strut portions 260 thereof). In the intervertebral cage 210 of FIG. 13, the axis or center of the first radius of the convex outer first radiused surface 262 may be offset in the posterior direction from the axis or center of the second radius of the concave interior second radiused surface 264 of the posterior member 216 (such as the first strut portions 260 thereof).

Figure 15:
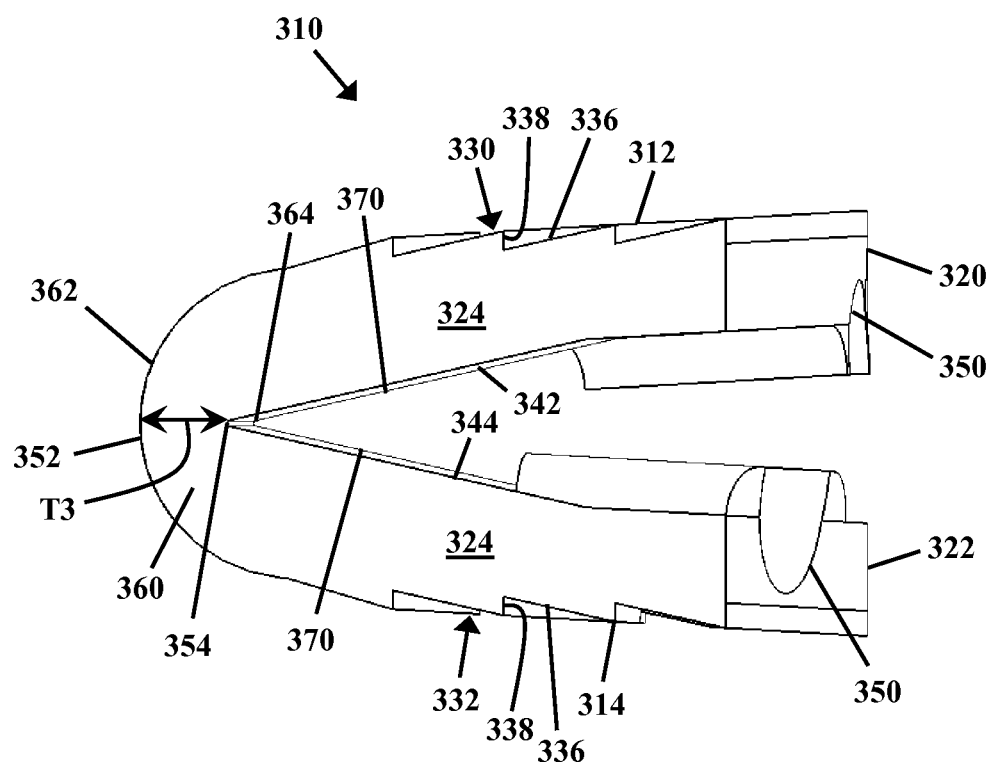
FIG. 15 is a lateral view of a fourth exemplary intervertebral cage of the present disclosure.

An embodiment of another intervertebral cage according to the present disclosures is shown in FIG. 15 and generally indicated with the reference numeral 310. Some aspects, elements and/or functions of exemplary intervertebral cage 310 may be the same or similar in structure and/or function, at least in part, to the intervertebral cage 10, 110 and 210 described above, and therefore at least some like reference numerals preceded by the numeral "3" are used to indicate at least some such potential similar aspects, elements and/or functions. One difference between intervertebral cage 310 of FIG. 14 and intervertebral cage 10, 110 and 210 may be the concave interior surface 64 of the posterior member 316 (such as the first strut portions 360 thereof). As shown in FIG. 15, the cage 310 includes a concave interior surface 364 of the posterior member 316 (such as the first strut portions 360 thereof) with a relatively small second radius (e.g., a chamfer), and substantially linear or planar segments 370 diverging therefrom in the superior-inferior direction as they extend in the posterior-to-interior direction to the first and second interior surfaces 342, 344 of the superior and inferior members 312, 314, respectively. In some such embodiments, the diverging substantially linear or planar segments 370 may diverge at acute angles from the transverse plane. In some such embodiments, the diverging substantially linear or planar segments 370 may form an acute angle therebetween as they extend in the posterior-to-interior direction.

Figure 16:
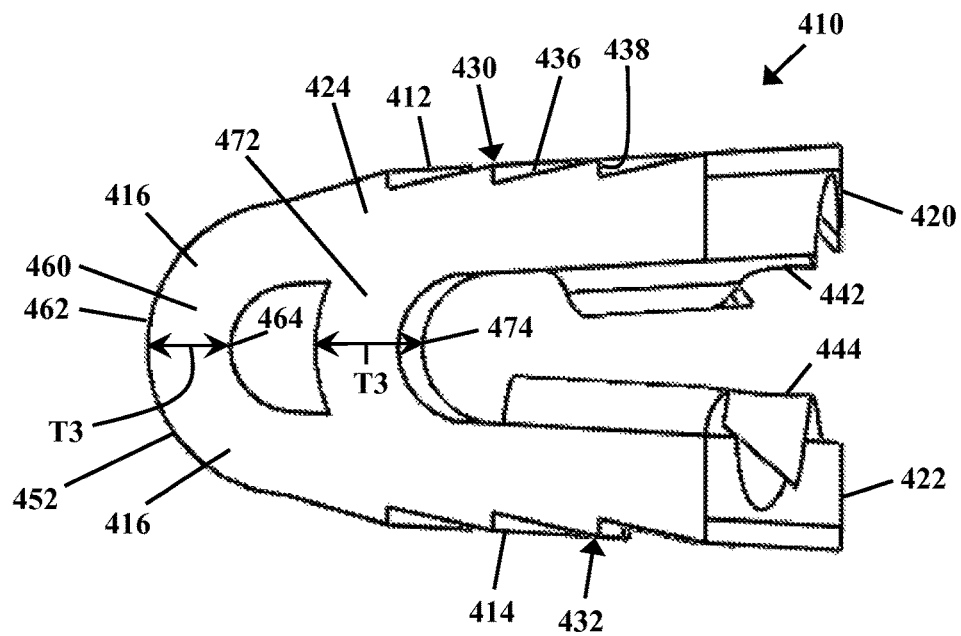
FIG. 16 is lateral view of a fifth exemplary intervertebral cage of the present disclosure.
Figure 17:
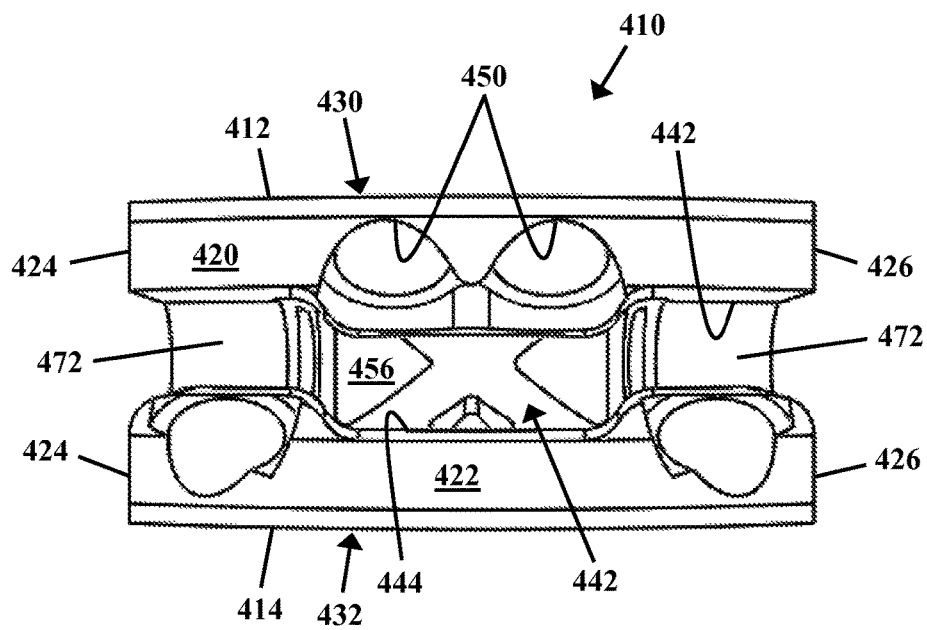
FIG. 17 is an anterior view of the fifth exemplary intervertebral cage of FIG. 16.

An embodiment of another intervertebral cage according to the present disclosures is shown in FIGS. 16 and 17 and generally indicated with the reference numeral 410. Some aspects, elements and/or functions of intervertebral cage 410 may be the same or similar in structure and/or function, at least in part, to the intervertebral cage 10, 110, 210 and 310 described above, and therefore at least some like reference numerals preceded by the numeral "4" are used to indicate at least some such potential similar aspects, elements and/or functions. One difference between intervertebral cage 410 of FIGS. 16 and 17 and intervertebral cage 10, 110, 210 and 310 may be the addition of second struts 472 positioned anterior to the posterior member 416 and between the first and second inferior surfaces 442, 444 of the superior and inferior member 412, 414, respectably. In some embodiments, the second struts 472 may be substantially similar in configuration to the first struts 460 portions of the posterior member 416. For example, the second struts 472 may define substantially the same width and orientation in the medial-lateral direction, substantially the same third thickness T3, and substantially the same convex and concave shape in the superior-inferior direction as the first struts 460 portions of the posterior member 416. Stated differently, in some embodiments the second struts 472 may only substantially differ from the first struts 460 portions of the posterior member 416 in their position in the anterior-posterior direction.

Another difference between intervertebral cage 410 of FIGS. 16 and 17 and intervertebral cage 10, 110, 210 and 310 may be the third thickness T3 of the posterior member 416 (e.g., the first strut portions 460) and the second struts 472. As shown in FIGS. 16 and 17, the third thickness T3 of at least the lateral side portions or first struts 460 of the posterior member 416 and the second struts 472 extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 1 millimeter and about 3 millimeters, or about 1 and ¾ millimeters. Some such cage 410 embodiments may be particularly advantageous for use with cervical vertebral bodies 434, 435. In some other embodiments, as shown in FIGS. 16 and 17, the thickness T3 of at least the lateral side portions or first struts 460 of the posterior member 416 and the second struts 472, extending between the furthest posterior-positioned exterior surface and the furthest anterior-positioned interior surface in the posterior-anterior direction (and/or measured along the transverse plane from the furthest posterior-positioned exterior surface) may be within the range of about ¼ millimeter and about 8 millimeters, or within the range of about 2 millimeter and about 5 millimeters, or about 3 millimeters. Some such cage 410 embodiments may be particularly advantageous for use with lumbar vertebral bodies 434, 435.

Figure 18:
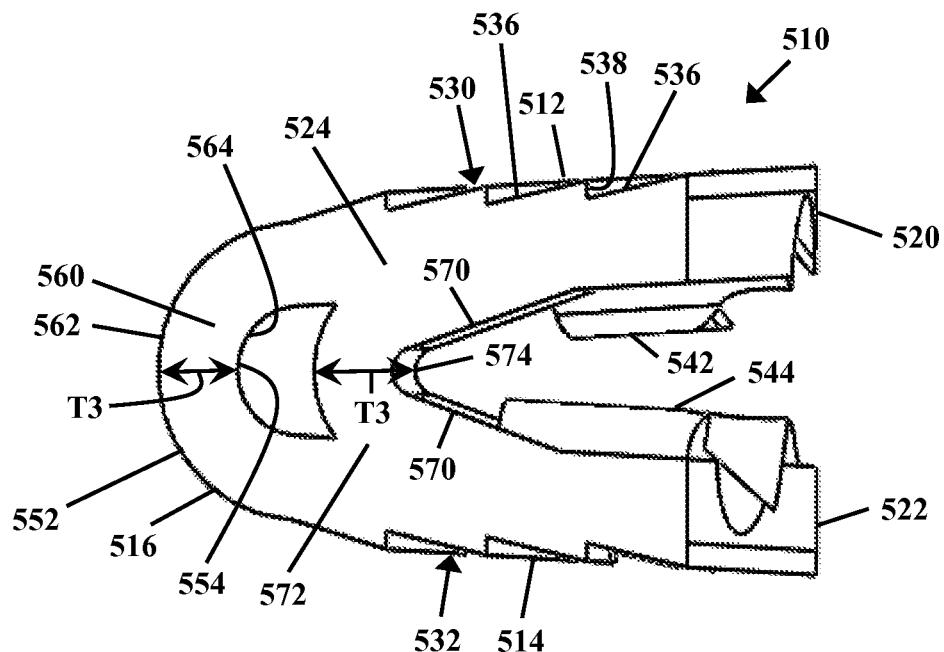
FIG. 18 is a lateral view of a sixth exemplary intervertebral cage of the present disclosure.
Figure 19:
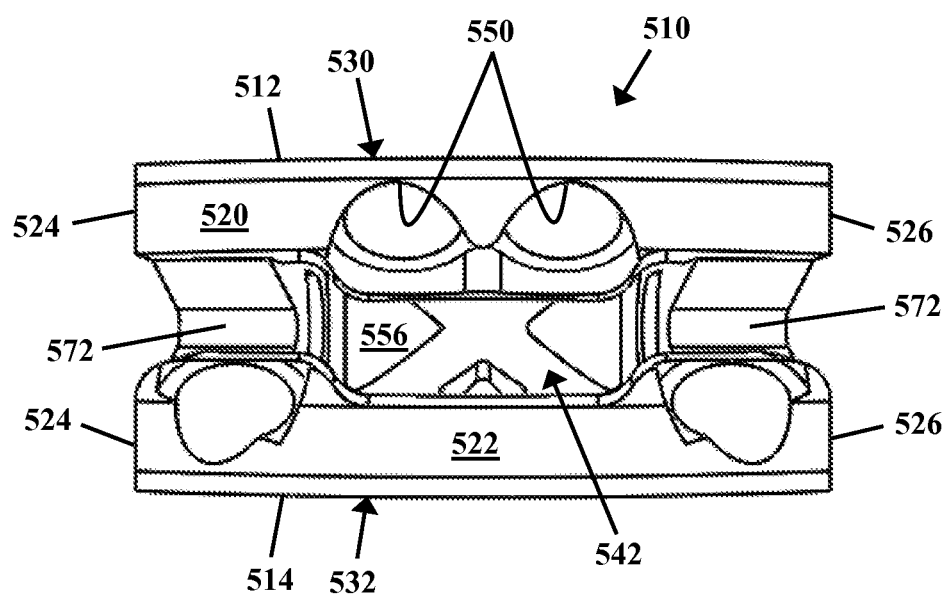
FIG. 19 is a front or anterior view of the sixth exemplary intervertebral cage of FIG. 18.
Figure 20:
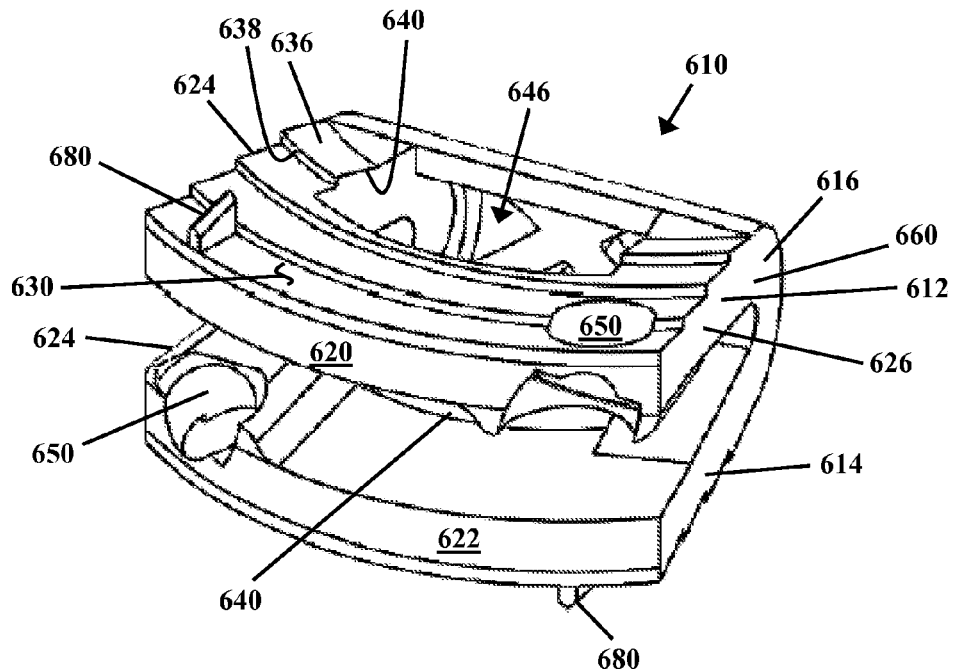
FIG. 20 is a superior perspective view of a seventh exemplary embodiment of an intervertebral cage of the present disclosure.
Figure 21:
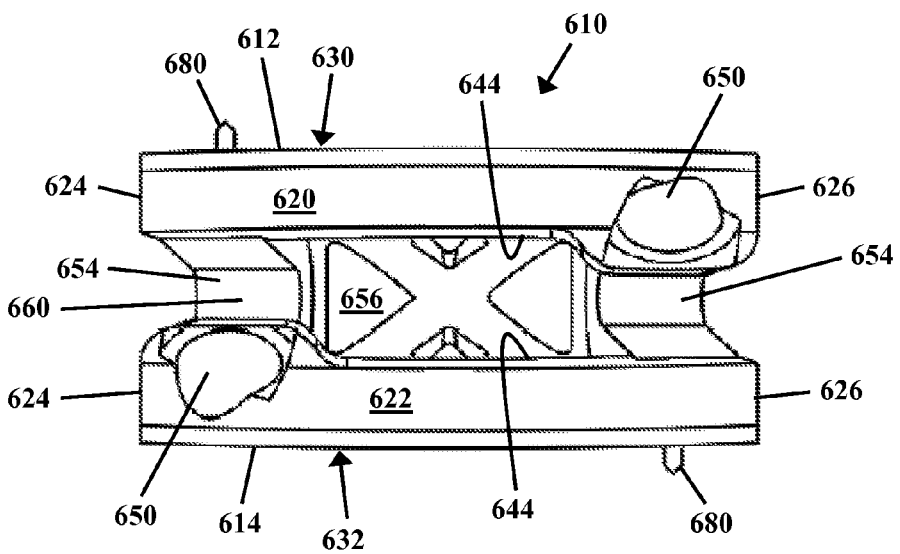
FIG. 21 is an anterior view of the seventh exemplary intervertebral cage of FIG. 20.
Figure 22:
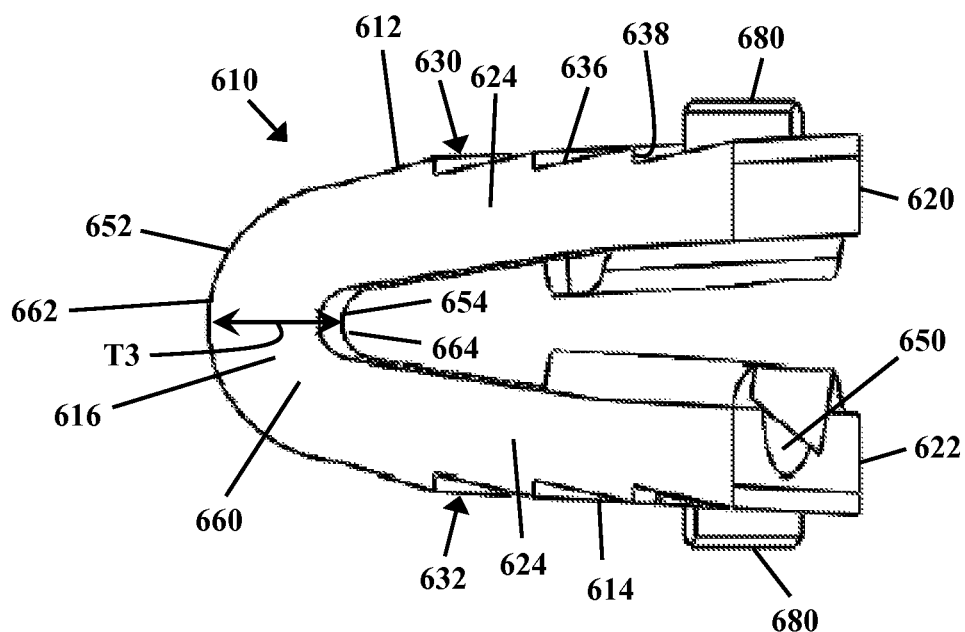
FIG. 22 is a lateral view of the seventh exemplary intervertebral cage of FIG. 20.
Figure 23:
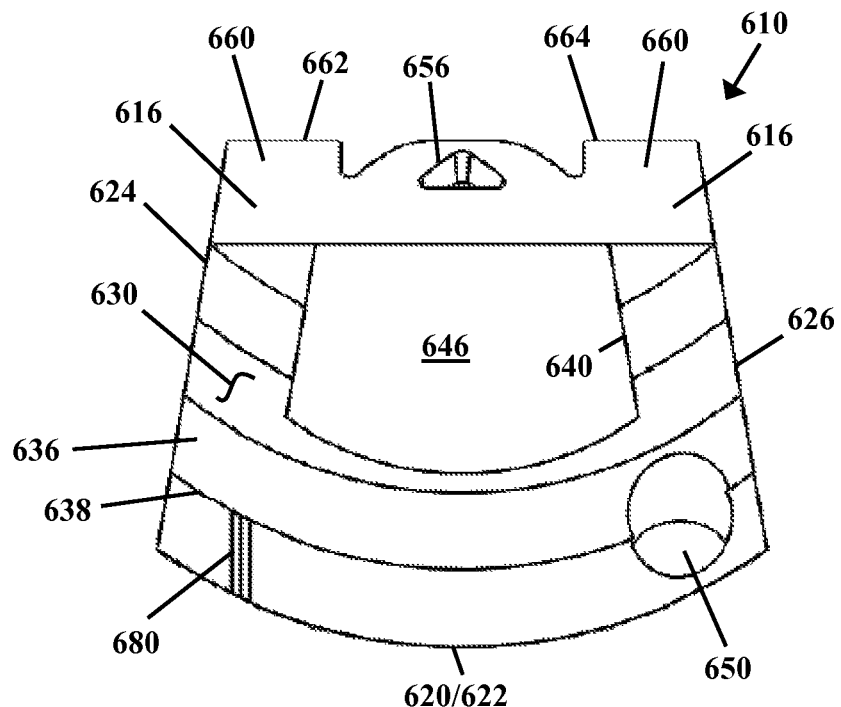
FIG. 23 is a superior view of the seventh exemplary intervertebral cage FIG. 20.

An embodiment of another intervertebral cage according to the present disclosures is shown in FIGS. 18 and 19 and generally indicated with the reference numeral 510. Intervertebral cage 510 is substantially similar to the intervertebral cage 410 of FIGS. 16 and 17 described above, and therefore at least some like reference numerals preceded by the numeral "5" are used to indicate at least some such potential similar aspects, elements and/or functions. One difference between intervertebral cage 510 of FIGS. 18 and 19 and intervertebral cage 410 of FIGS. 16 and 17 may be the configuration of the second struts 572. As shown in FIGS. 18 and 19, the concave interior third surface 574 of the second struts 572 may differ from the concave interior second radiused surface 64 of the posterior member 16, such as the first strut portions 560 thereof. For example, the concave interior third surface 574 of the second struts 572 may define or include a third radius of curvature that is less than the second radius of the concave interior second radiused surface 564 of the first strut portions 560. In some embodiments, the third radius of the concave interior third radiused surface 574 of the second struts 572 may be within the range of about ¼ millimeter and about 15 millimeters, or within the range of about ¼ millimeter and about 2 and ½ millimeters, or about ½ millimeter. Some such cage 510 embodiments may be advantageous with cervical vertebral bodies 534, 535. In some other embodiments, the a third radius of the concave interior third radiused surface 574 of the second struts 572 may be within the range of about ¼ millimeter and about 20 millimeters, or within the range of about 1 millimeter and about 5 millimeters, or about 1 millimeters. Some such cage 510 embodiments may be have advantages for use with lumbar vertebral bodies 534, 535.

As shown in FIGS. 18 and 19, the concave interior third surface 574 of the second struts 572 also includes or defines linear or planar segments 570 that extend from the concave interior third radiused surface and diverge in the superior-inferior direction as they extend in the posterior-to-interior direction to the first and second interior surfaces 542, 544 of the superior and inferior members 512, 514, respectively. In some such embodiments, the diverging substantially linear or planar segments 570 may diverge at acute angles from the transverse plane. In some such embodiments, the diverging segments 570 may form an acute angle therebetween as they extend in the posterior-to-interior direction.

An embodiment of another intervertebral cage according to the present disclosures is shown in FIGS. 20-23 and generally indicated with the reference numeral 610. Some aspects, elements and/or functions of intervertebral cage 610 may be the same or similar in structure and/or function, at least in part, to the intervertebral cages 10, 110, 210, 310, 410 and 510 described above, and therefore at least some like reference numerals preceded by the numeral "6" are used to indicate at least some such potential similar aspects, elements and/or functions. One difference between exemplary intervertebral cage 610 of FIGS. 20-23 and exemplary intervertebral cages 10, 110, 210, 310, 410 and 510 may be the addition at least one engagement member 680 extending from at least one of the first engagement surface 630 of the superior member 612 and the second engagement surface 632 of the inferior member 614 at least generally in the superior-inferior direction. The at least one engagement member 680 may take any form, shape or configuration effective in engaging the superior or inferior vertebrae in which the cage 610 may be implanted. In some embodiments, the at least one engagement member 680 may be configured to penetrate or otherwise extend into the superior or inferior vertebrae 634, 635. In some embodiments, the at least one engagement member 680 may take the form of a spike, nail, keel, rod, cone, tooth or the like. In some embodiments, as shown in FIGS. 20-23, the at least one engagement member 680 may extend away from at least one of the first engagement surface 630 of the superior member 612 and the second engagement surface 632 of the inferior member 614 in the inferior-superior direction, and may end along the medial-lateral and posterior-anterior direction. In some such embodiments, the free end of the at least one engagement member 680 may be angled in the medial-to-lateral and lateral-to-medial directions to form a tip. In some such embodiments, the free end of the at least one engagement member 680 may be angled in the superior-to-anterior direction as it extends in the posterior-to-anterior direction. Such a configuration may act to prevent the cage 610 from backing out in the posterior-to-anterior direction after it is implanted.

As also shown in FIGS. 20-23, the at least one engagement member 680 may be provided proximate the second free ends 620, 622 of at least one of the first engagement surface 630 of the superior member 612 and the second engagement surface 632 of the inferior member 614. For example, at least one engagement member 680 may be positioned proximate of the junctions of the lateral sides 624, 626 of the superior member 612 and inferior member 614 and the second free ends 620, 622 thereof, as shown in FIGS. 20-23. In some embodiments, as shown in FIGS. 20-23, the cage 610 may include at least one engagement member 680 and at least one second aperture 650 provided on the superior member 612 and/or inferior member 614. For example, in some embodiments the superior member 612 and/or inferior member 614 may include an at least one engagement member 680 proximate the junction of one lateral side 624, 626 and the free ends 620, 622 thereof and a second aperture 650 at the junction of the opposing lateral side 624, 626 and the free end 620, 622 thereof. In some embodiments the superior and inferior members 612, 614 may each include at least one engagement member 680 and at least one second aperture 650, and at least one engagement member 680 of the superior member 612 may be aligned along the superior-inferior direction with a second aperture 650 of the inferior member 614, and an at least one engagement member 680 of the inferior member 614 may be aligned along the superior-inferior direction with a second aperture 650 of the superior member 612.

Figure 24:
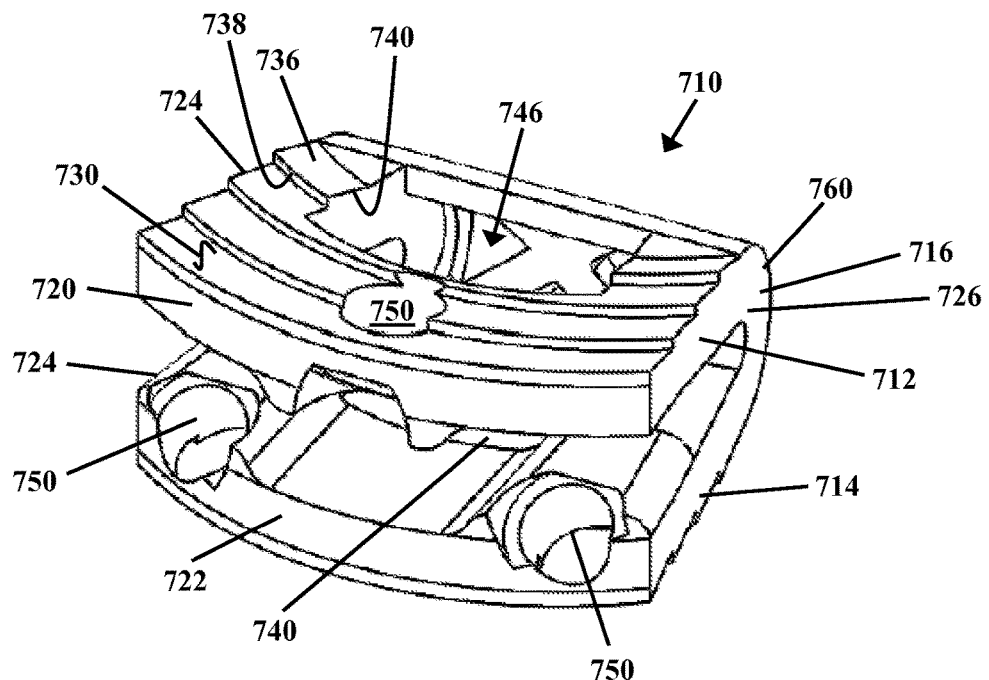
FIG. 24 is a superior perspective view of an eighth exemplary embodiment of an intervertebral cage of the present disclosure.
Figure 25:
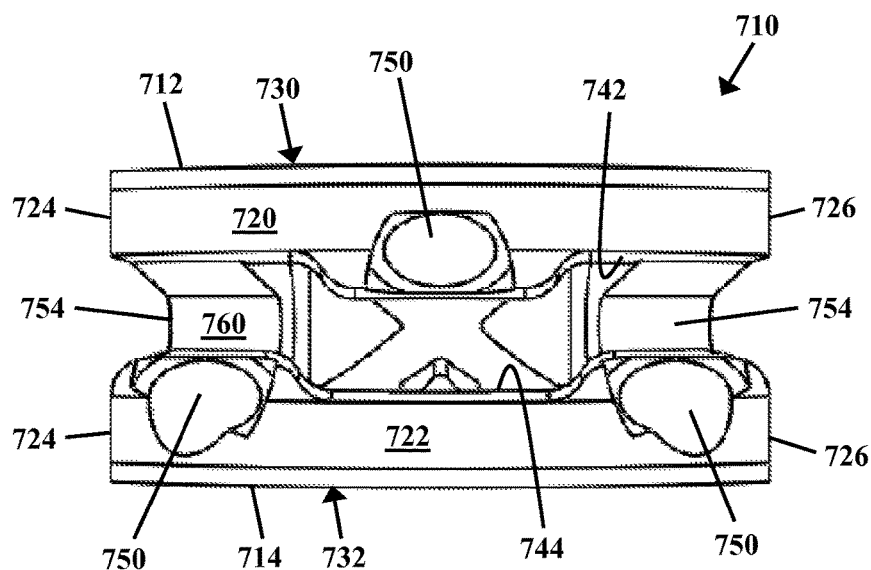
FIG. 25 is an anterior view of the eighth exemplary intervertebral cage of FIG. 24.

An embodiment of another intervertebral cage according to the present disclosures is shown in FIGS. 24 and 25 and generally indicated with the reference numeral 710. Some aspects, elements and/or functions of intervertebral cage 710 may be the same or similar in structure and/or function, at least in part, to the intervertebral cage 10, 110, 210, 310, 410, 510 and 610 described above, and therefore at least some like reference numerals preceded by the numeral "7" are used to indicate at least some such potential similar aspects, elements and/or functions. One difference between intervertebral cage 710 of FIGS. 24 and 25 and exemplary intervertebral cage 10, 110, 210, 310, 410, 510 and 610 may be the configuration of the second aperture 750. As shown in FIGS. 24 and 25, the cage 710 may include any number of potential configurations of second aperture 750 through the superior and/or inferior members 712, 714. As one arrangement, the cage 710 includes three of the second aperture 750. As shown in FIGS. 24 and 25, the superior member 712 (or the inferior member 714) may include one second aperture 750 proximate the second free end 620 thereof in a medial portion in the medial-lateral direction. In some such embodiments, the medially-positioned second aperture 750 of the superior member 712 (or the inferior member 714) may extend in an anterior-to-posterior direction as it extends in an inferior-to-superior direction. The medially-positioned second aperture 750 of the superior member 712 (or the inferior member 714) may also be angled in the medial direction, or may extend lineally in a direction along the sagittal plane. As also shown in FIGS. 24 and 25, the inferior member 714 (or the superior member 712) may include a pair of second apertures 750, 750 spaced along the medial-lateral direction from each other and the medially-positioned second aperture 750 of the superior member 712 (or the inferior member 714), as described above. Such pair of second apertures 750, 750 spaced along the medial-lateral direction may converge in the medial-lateral direction as they extend in a superior-to-inferior direction.

Figure 26:
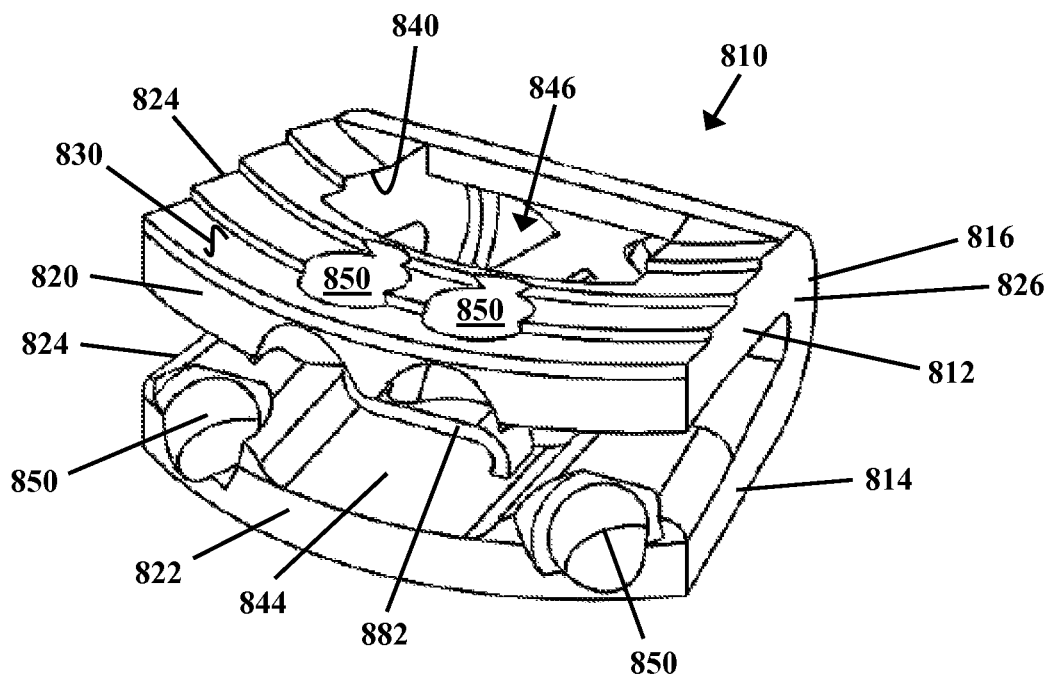
FIG. 26 is a superior view of a ninth exemplary embodiment of an intervertebral cage of the present disclosure.
Figure 27:
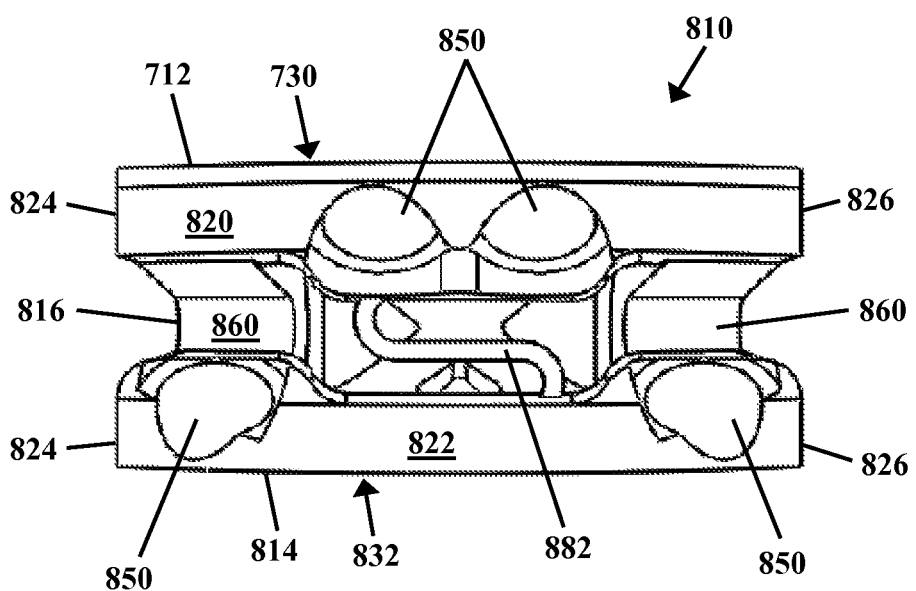
FIG. 27 is an anterior view of the ninth exemplary intervertebral cage FIG. 26.
Figure 28:
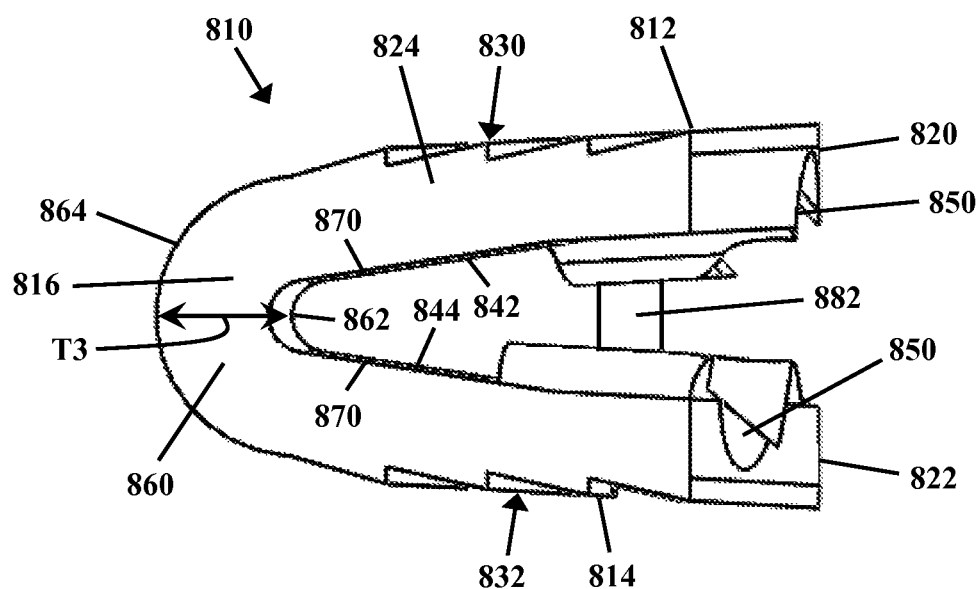
FIG. 28 is a lateral view of the ninth exemplary intervertebral cage of FIG. 26.
Figure 29:
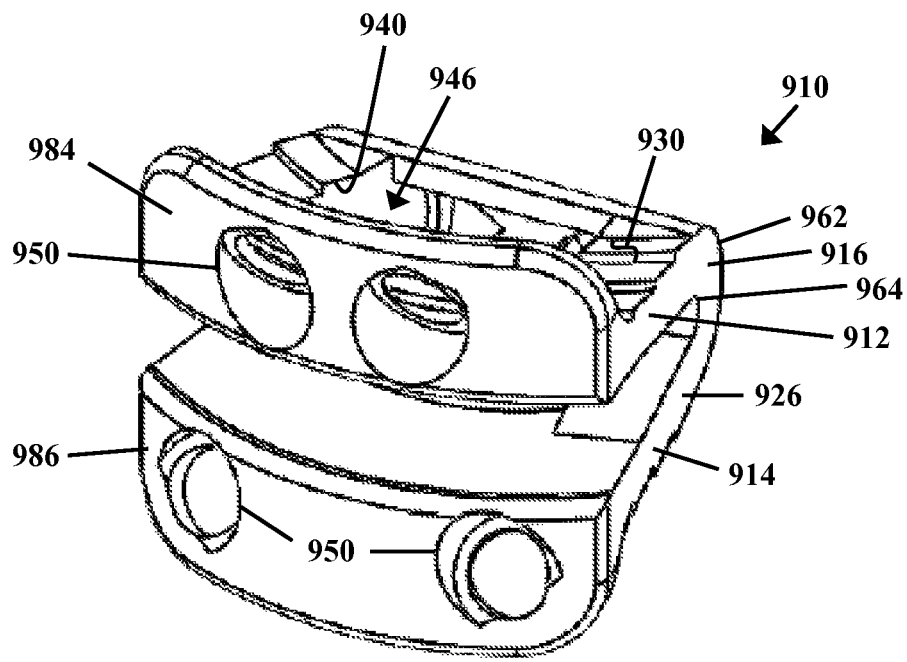
FIG. 29 is a superior perspective view of a tenth exemplary embodiment of an intervertebral cage of the present disclosure.
Figure 30:
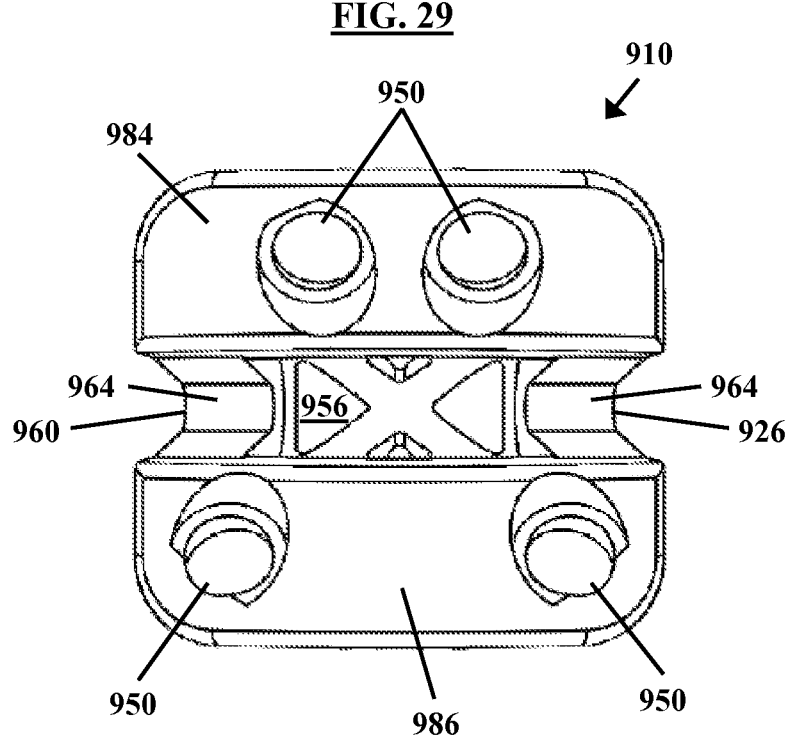
FIG. 30 is an anterior view of the tenth exemplary intervertebral cage FIG. 29.
Figure 31:
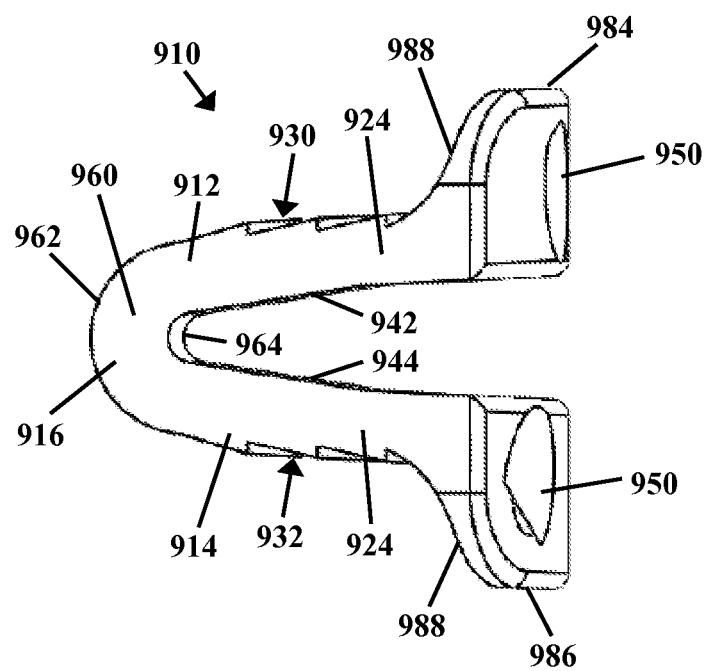
FIG. 31 is a lateral view of the tenth exemplary intervertebral cage FIG. 29.
Figure 32:
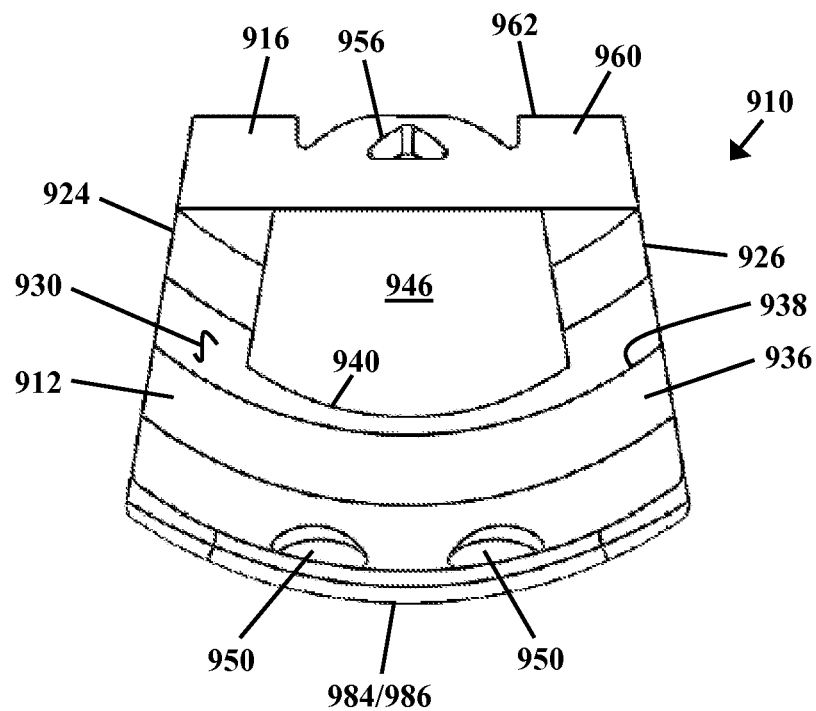
FIG. 32 is a superior view of the tenth exemplary intervertebral cage of FIG. 29.

An embodiment of another intervertebral cage according to the present disclosures is shown in FIGS. 26-28 and generally indicated with the reference numeral 810. Some aspects, elements and/or functions of intervertebral cage 810 may be the same or similar in structure and/or function, at least in part, to the exemplary intervertebral cage 10, 110, 210, 310, 410, 510, 610 and 710 described above, and therefore at least some like reference numerals preceded by the numeral "8" are used to indicate at least some such potential similar aspects, elements and/or functions. One difference between intervertebral cage 810 of FIGS. 26-28 and exemplary intervertebral cage 10, 110, 210, 310, 410, 510, 610 and 710 may be the inclusion of at least one resilient member 882 882 between the superior and inferior member 812, 814 in medial-lateral, posterior-anterior and superior-inferior directions. The at least one resilient member 882 may be any resilient member(s) 882, such as an elastically deforming load bearing member(s). For example the at least one resilient member 882 may include a struts, ovoids, springs, or any other member effective in control the movement of the superior and inferior member 812, 814 with respect to one another, such as along the inferior-superior direction. In some embodiments, the at least one resilient member 882 may be a serpentine spring that extends in the medial-lateral and superior-inferior directions. In some other embodiments, the at least one resilient member 882 may be a serpentine spring that extends in the posterior-anterior and superior-inferior directions.

As shown in FIGS. 26-28, in some embodiments the at least one resilient member 882 may end between the second interior surfaces 842, 844 of the superior member 812 and the inferior member 814 in the superior-inferior direction, and may be paced from the posterior member 816 in the posterior-to-anterior direction. As also shown in FIGS. 26-28, in some embodiments the at least one resilient member 882 may be positioned posterior to the first apertures 840 of the superior member 812 and the inferior member 814, and in a medial portion of the superior member 812 and the inferior member 814 in a medial-lateral direction. In some embodiments, the at least one a resilient member 882 may be positioned between the superior member 812 and the inferior member 814 in the superior-inferior direction, anterior to the first pathway 846, and posterior to the anterior free second ends 820, 822 of the superior member 812 and the inferior member 814.

An embodiment of another intervertebral cage according to the present disclosures is shown in FIGS. 29-32 and generally indicated with the reference numeral 910. Some aspects, elements and/or functions of intervertebral cage 910 may be the same or similar in structure and/or function, at least in part, to the exemplary intervertebral cage 10, 110, 210, 310, 410, 510, 610, 710 and 810 described above, and therefore at least some like reference numerals preceded by the numeral "9" are used to indicate at least some such potential similar aspects, elements and/or functions. One difference between intervertebral cage 910 of FIGS. 29-32 and exemplary intervertebral cage 10, 110, 210, 310, 410,

510, 610, 710 and 810 may be the inclusion of anterior wing members 984, 986 extending from the anterior free second ends 920, 922 of the superior member 912 and inferior member 914. As shown in FIGS. 29-32, the exemplary wing members 984, 986 may extend away from the first or second engagement surfaces 930, 932 of the corresponding superior or inferior member 914 in the inferior direction. For example, a first wing member 984 associated with the superior member 912 may extend substantially in the inferior-to-superior direction from the second free end 920 of the superior member 912, and a second wing member 986 associated with the inferior member 914 may extend substantially in the superior-to-inferior direction from the second free end 922 of the inferior member 914. In this way, the first and second wing members 984, 986 may each include or define a posterior-facing engagement surface 988 that may be configured to engage or abut a corresponding an anterior-facing surface of the vertebrae bodies 934, 936 between which other portions of the cage 910 may be implanted. In this way, the first and second wing members 984, 986 may not be positioned between the vertebrae bodies 934, 936 when the cage 910 is implanted.

As also shown in FIGS. 29-32, the second apertures 950 may pass through the wing members 984, 986 as opposed to the superior and inferior members 912, 914. The second apertures 950 may include the same or similar pattern and configuration as described above. For example, the second apertures 950 of the first and second wing members 984, 986 may be angled in the medial lateral direction to converge or diverge. Similarly, the at least one second aperture 950 of the first and second wing members 984, 986 may be angled in the posterior direction from the superior-inferior direction.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the embodiments described herein may be embodied or carried out in a manner that achieves or optimizes one advantage or group of advantages as taught herein without necessarily achieving other objects or advantages as may be taught or suggested.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An intervertebral cage, comprising:
    a superior member including a first engagement surface for engaging a superior vertebrae;
    an inferior member including a second engagement surface for engaging an inferior vertebrae;
    a posterior member extending between a first end of the superior member and a first end of the inferior member, the posterior member spacing the first ends of the superior member and the inferior member in a superior-inferior direction,
    wherein the superior member and the inferior member extend in a posterior-to-anterior direction from the posterior member and define anterior free second ends to form an open anterior end between the superior member and the inferior member in a posterior-anterior direction,
    wherein the first engagement surface of the superior member and the second engagement surface of the inferior member substantially diverge from each other in the superior-inferior direction along the posterior-to-anterior direction from the posterior member to the free second ends thereof,
    wherein the superior member and the inferior member each include first apertures extending therethrough in the superior-inferior direction that at least partially overlap in the superior-inferior direction and define a first pathway through the intervertebral cage in the superior-inferior direction,
    wherein the superior member has a first thickness in the superior-inferior direction,
    wherein the inferior member has a second thickness in the superior-inferior direction, and
    wherein the posterior member has a third thickness in the anterior-posterior direction and the third thickness is larger than the first thickness and the second thickness.

2. The intervertebral cage of claim 1, wherein the first engagement surface of the superior member and the second engagement surface of the inferior member substantially diverge from each other along the superior-inferior direction in the posterior-to-anterior direction at an angle less than about 13 degrees.

3. The intervertebral cage of claim 1, wherein each of the superior member and the inferior member extend in a medial-lateral direction and define opposing lateral ends that are aligned in the superior-inferior direction, and wherein a distance between the lateral ends of the superior member and the inferior member in the medial-lateral direction is greater at the free second ends than at the first ends thereof.

4. The intervertebral cage of claim 1, wherein the superior member includes a first interior surface opposing the first engagement surface in the superior-inferior direction, and the superior member includes at least one second aperture proximate the anterior free second end thereof extending through the superior member in the superior-inferior direction and angled in an anterior-to-posterior direction and along a medial-lateral direction from the first interior surface to the first engagement surface.

5. The intervertebral cage of claim 1, wherein the inferior member includes a second interior surface opposing the second engagement surface in the superior-inferior direction, and the inferior member includes at least one second aperture proximate the anterior free second end thereof extending through the inferior member in the superior-inferior direction and angled in an anterior-to-posterior direction and along a medial-lateral direction from the second interior surface to the second engagement surface.

6. The intervertebral cage of claim 1, wherein each of the superior member and the inferior member include at least one second aperture proximate the anterior free second ends thereof extending through the superior member and the inferior member in the superior-inferior direction, and wherein the at least one second aperture of the superior member and the at least one second aperture of the inferior member are off-set along the medial-lateral direction with respect to each other.

7. The intervertebral cage of claim 6, wherein the thicknesses of each of the superior member and the inferior member extending about the at least one second aperture thereof is greater than other thicknesses of the superior member and the inferior member in the superior-inferior direction.

8. The intervertebral cage of claim 1, wherein the free second end of each of the superior member and the inferior member is convex in the posterior-to-anterior direction.

9. The intervertebral cage of claim 1, wherein the posterior member is substantially convex and extends in an anterior-to-posterior direction defining a convex exterior surface and a concave interior surface.

10. The intervertebral cage of claim 9, wherein the posterior member includes at least one aperture that extends through the posterior member in the posterior-anterior direction.

11. The intervertebral cage of claim 9, wherein the third thickness of the posterior member extends between a furthest posterior-positioned portion of each of the convex outer surface and the concave interior surface.

12. The intervertebral cage of claim 11, wherein the third thickness is between about ¼ millimeter and about 8 millimeters.

13. The intervertebral cage of claim 9, wherein the concave interior surface of the posterior member and the interior surface of at least one of the superior member and inferior member form an acute angle.

14. The intervertebral cage of claim 9, wherein the concave interior surface of the posterior member forms a first radiused surface defined by a first radius between about ¼ millimeter and about 20 millimeters.

15. The intervertebral cage of claim 14, wherein the convex outer surface of the posterior member forms a second radiused surface defined by a second radius that is greater than the first radius.

16. The intervertebral cage of claim 15, wherein the first radiused surface and the second radiused surface are concentric.

17. The intervertebral cage of claim 15, wherein an axis of the first radius and an axis of the second radius are offset in the posterior-anterior direction.

18. The intervertebral cage of claim 1, wherein the superior member and inferior member each define lateral sides in the medial-lateral direction, and wherein the intervertebral cage includes a strut member extending between the superior member and the inferior member in the superior-inferior direction positioned proximate each of the lateral sides of the superior and inferior members and spaced from the posterior member in the posterior-to-anterior direction.

19. The intervertebral cage of claim 1, further including at least one resilient member extending between the superior member and the inferior member in the superior-inferior direction and spaced from the posterior member in the posterior-to-anterior direction.

20. The intervertebral cage of claim 19, wherein the at least one resilient member is positioned anterior to the first apertures of the superior member and the inferior member, and in a medial portion of the superior member and the inferior member in a medial-lateral direction.

21. The intervertebral cage of claim 1, wherein each of the superior member and the inferior member include at least one second aperture extending through the superior member and the inferior member in the superior-inferior direction, and wherein each of the superior member and the inferior member include at least one engagement member extending away from the first engagement surface and the second engagement surface, respectively, in the superior-inferior direction.

22. The intervertebral cage of claim 21, wherein each of the superior member and the inferior member extend in a medial-lateral direction and define opposing lateral ends substantially aligned along the superior-inferior direction, and wherein the at least one second apertures and the at least one engagement members are each positioned proximate a junction of the anterior free second ends and the lateral ends of the superior and inferior members.

23. The intervertebral cage of claim 22, wherein an engagement member of the superior member is substantially aligned with a second aperture of the inferior member along the superior-inferior direction, and wherein an engagement member of the inferior member is substantially aligned with a second aperture of the superior member along the superior-inferior direction.

24. The intervertebral cage of claim 1, wherein the first and second engagement surfaces include a ridge pattern comprising a plurality of ridge portions and relief portions.

25. The intervertebral cage of claim 24, wherein a first ridge portion of the superior member is adjacent to a second ridge portion along the posterior-anterior direction, and at least partially positioned superior to the second ridge portion, and wherein a relief portion extends between the superior-positioned portion of the first ridge portion to the anterior-positioned portion of the second ridge portion.

26. The intervertebral cage of claim 24, wherein the ridge portions of the ridge pattern of the superior member extend in the posterior-to-anterior direction and in an inferior-to-superior direction in the posterior-to-anterior direction, and wherein the ridge portions of the ridge pattern of the inferior member extend in the posterior-to-anterior direction and in the superior-to-inferior direction in the posterior-to-anterior direction.

27. The intervertebral cage of claim 26, wherein the relief portions of the ridge pattern of the superior member extend at least in the superior-to-inferior direction, and wherein the relief portions of the ridge pattern of the inferior member extend at least in the inferior-to-superior direction.

28. The intervertebral cage of claim 26, wherein the ridge portions and relief portions of the ridge pattern are arcuate in a medial-lateral direction.

29. The intervertebral cage of claim 26, wherein the ridge portions and relief portions of the ridge pattern extend substantially linearly along a medial-lateral direction.

30. The intervertebral cage of claim 1, wherein the posterior member includes at least one aperture extending therethrough in the posterior-anterior direction.

31. The intervertebral cage of claim 1, wherein the intervertebral cage is of one-piece construction.

32. The intervertebral cage of claim 1, wherein the superior member, inferior member, and posterior member are integral.

33. The intervertebral cage of claim 1, further including a bone graft material positioned at least partially within the first pathway.

34. The intervertebral cage of claim 1, further including at least one bone fixation device extending through the superior member proximate the anterior free second end thereof in the superior-inferior direction, and including at least one bone fixation device extending through the inferior member proximate the anterior free second end thereof in the superior-inferior direction.

35. The intervertebral cage of claim 1, wherein the first pathway defines a surface area in a transverse plane of at least about 15% of a surface area of at least one of the first engagement surface and the second engagement surface.

36. The intervertebral cage of claim 1, wherein the first pathway defines a surface area in a transverse plane of at least about 30 square millimeters.

37. The intervertebral cage of claim 1, wherein the first pathway defines a surface area in a transverse plane of at least about 50 square millimeters.

* * * * *